US012691109B2

(12) United States Patent
Tang et al.

(10) Patent No.: US 12,691,109 B2

(45) Date of Patent: Jul. 28, 2026

(54) BIFUNCTIONAL AGGREGATION-INDUCED EMISSION LUMINOGEN FOR MONITORING AND KILLING OF MULTIDRUG-RESISTANT BACTERIA

(71) Applicant: The Hong Kong University of Science and Technology, Hong Kong (CN)

(72) Inventors: Benzhong Tang, Hong Kong (CN); Ying Li, Hong Kong (CN); Zheng Zhao, Hong Kong (CN)

(73) Assignee: THE HONG KONG UNIVERSITY OF SCIENCE AND TECHNOLOGY, Hong Kong (CN)

( * ) Notice: Subject to any disclaimer, the term of this patent is extended or adjusted under 35 U.S.C. 154(b) by 964 days.

(21) Appl. No.: 17/260,075

(22) PCT Filed: Jul. 11, 2019

(86) PCT No.: PCT/CN2019/095581

§ 371 (c)(1),
(2) Date: Jan. 13, 2021

(87) PCT Pub. No.: WO2020/011228

PCT Pub. Date: Jan. 16, 2020

(65) Prior Publication Data

US 2021/0290611 A1 Sep. 23, 2021

Related U.S. Application Data

(60) Provisional application No. 62/763,979, filed on Jul. 13, 2018.

(51) Int. Cl.

| | |
|---|---|
| ***A61K 31/473*** | (2006.01) |
| ***A61K 49/00*** | (2006.01) |

(Continued)

(52) U.S. Cl.

CPC ........ *A61K 31/473* (2013.01); *A61K 49/0021* (2013.01); *C09K 11/06* (2013.01)

(58) Field of Classification Search

CPC .. A61K 31/473; A61K 49/0021; C09K 11/06; A61P 31/04; C07D 401/06

See application file for complete search history.

(56) References Cited

U.S. PATENT DOCUMENTS 6,967,023 B1 * 11/2005 Eini ........................ A61P 35/00 424/78.06

FOREIGN PATENT DOCUMENTS

| | | |
|---|---|---|
| CN | 102706839 A | 10/2012 |
| CN | 106461641 A | 2/2017 |

(Continued)

OTHER PUBLICATIONS

Yu et al., Synthesis of Solution Processable Blue AIEgens and the Device Performance, Acta Chim. Sinica, 74, pp. 865-870 (Year: 2016).*

(Continued)

*Primary Examiner* — Jeffrey S Lundgren
*Assistant Examiner* — Alexander K. Showalter
(74) *Attorney, Agent, or Firm* — Nath, Goldberg & Meyer; Joshua B. Goldberg

(57) ABSTRACT

Antibiotic compounds having both antibiotic and aggregation-induced emission (AIE) characteristics. The compounds comprise an azole antibiotic unit, for example naphthalimide triazole (NT), and an AIE unit, for example triphenylethylene (TriPE). The compounds act as an effective AIEgen with ROS generating capabilities. The present combinations of an azole antibiotic unit and an AIE unit do not negatively affect the antibacterial properties of the azole. Accordingly, the present compounds exterminate bacteria with both the antibacterial mechanism of the azole along (Continued)

with the ROS produced when the AIE unit is exposed to light. In addition, the intrinsic imagining ability of the present compounds enables them to be used as imaging tools to monitor the drug-bacteria interaction. Collectively, the present compounds provide multiple functions including imaging, monitoring, and bacterial infection inhibition for integrated diagnosis and treatment in clinical practices.

9 Claims, 29 Drawing Sheets

(51) Int. Cl.

| | |
|---|---|
| ***A61P 31/04*** | (2006.01) |
| ***C07D 401/06*** | (2006.01) |
| ***C09K 11/06*** | (2006.01) |

(56) References Cited

FOREIGN PATENT DOCUMENTS

| | | | |
|---|---|---|---|
| CN | 107602469 | A | 1/2018 |
| WO | 2016078603 | A | 5/2016 |

OTHER PUBLICATIONS

Tian et al., Construction of a tetraphenylethene derivative exhibiting high contrast and multicolored emission switching, J. Mater. Chem. C, 5, 12785-12791 (Year: 2017).*

Feng et al., A light-up probe with aggregation-induced emission characteristics (AIE) for selective imaging, naked-eye detection and photodynamic killing of Gram-positive bacteria, Chem. Commun., 51, pp. 12490-12493 (Year: 2015).*

Synthesis of Solution Processable Blue AlEgens and the Device Performance, Acta Chim. Sinica, 74, pp. 865-870 (Year: 2016).*

Damu et al., A series of naphthalimide azoles: Design, synthesis and bioactive evaluation as potential antimicrobial agents, Science China: Chem., 56, pp. 952-969 (Year: 2015).*

Feng et al., A light-up probe with aggregation-induced emission characteristics (AIE) for selective imaging, naked-eye detection and photodynamic killing of Gram-positive bacteria, Chem. Commun., 51, pp. 12490-1249 (Year: 2015).*

Zhang et al., Utilising tetraphenylethene as a dual activator for intramolecular charge transfer and aggregation induced emission, Chem. Commun., 48, pp. 7711-7713 (Year: 2012).*

Peng et al., Synthesis of 1,4-Bis[2,2-bis(4-alkoxyphenyl)vinyl]benzenes and Side Chain Modulation of Their Solid-State Emission, Org. Lett., 12, pp. 4364-4367 (Year: 2010).*

Yu et al., Synthesis of Solution Processable Blue AlEgens and the Device Performance, Acta Chim. Sinica, 74, pp. 865-870 (Year: 2016).*

Zhang Y.Y. et al., "Synthesis and activities of naphthalimide azoles as a new type of antibacterial and antifungal agents," Bioorganic & Medicinal Chemistry Letters, May 18, 2011, vol. 21, pp. 4349-4352 (only English abstract attached).

Zhang G.F. et al., "Utilising tetraphenylethene as a dual activator for intramolecular charge transfer and aggregation Induced emission," Chem. Commun., Dec. 31, 2012, vol. 48, pp. 7711-7713.

* cited by examiner

BIFUNCTIONAL AGGREGATION-INDUCED EMISSION LUMINOGEN FOR MONITORING AND KILLING OF MULTIDRUG-RESISTANT BACTERIA

FIELD

The present subject matter relates generally to an antibiotic agent for treating diseases caused by bacteria which also acts as a fluorescent agent for monitoring bacterial infections and further exploring the related antibacterial mechanism.

BACKGROUND

Multidrug-resistant (MDR) bacteria pose serious threats to public health due to the lack of biocompatible antibiotics that can effectively kill the MDR bacteria. With the emergence of drug-resistance against existing antibiotics, it is of utmost urgency to develop new therapeutic agents. Photodynamic therapy (PDT) is a potential alternative to antibiotics for killing bacteria. In general, PDT employs photosensitizers (PSs) to absorb light and generate a single excited state ($S_1$). The $S_1$ state can further transfer the energy to a triplet excited state (Ti), which would sensitize the ambient triplet oxygen, resulting in formation of the destructive singlet oxygen or other reactive oxygen species (ROS). PDT can target both external and internal structures of bacteria, and without requiring the PSs to enter bacteria; thus, the sterilization mechanism of PDT is different from traditional antibiotics. Therefore, bacteria can hardly develop resistance to PDT. However, most of the PSs reported so far are hydrophobic and tend to form aggregates when they interact with bacteria in physiological hydrophilic conditions. Such molecular aggregation could cause the quenching of the singlet state, which thus quenches the fluorescence and also reduces ROS generation and compromises the effects of both imaging and therapy. In comparison with traditional PSs, organic luminogens with aggregation-induced emission characteristics (AIEgens) are a kind of molecules showing faint or no emission in solution, but enhanced emission upon aggregation. The unique aggregated lit-up fluorescence characteristic of AIEgens enables their extensive bio-imaging applications. More importantly, some AIEgens were found to exhibit aggregation enhanced ROS generation property, suggesting their application in image-guided PDT. Until now, several AIEgens have been reported for imaging or killing bacteria, however, these reported AIEgens mostly are mono-functional and their antibacterial ability is not systematically investigated. So, it remains an open question as to whether it is possible to integrate antibiotics with PDT to generate powerful novel super-antibiotics to combat with bacteria or even MDR bacteria.

Accordingly, antibiotic compounds which integrate PDT and traditional therapies are highly desirable.

SUMMARY

The present subject matter relates to compounds having antibiotic and aggregation-induced emission (AIE) characteristics. The compounds comprise an azole antibiotic unit, for example a naphthalimide triazole (NT), and an AIE unit, for example triphenylethylene (TriPE). The compounds act as an effective AIEgen with ROS generating capabilities. The present combinations of an azole antibiotic unit and an AIE unit do not negatively affect the antibacterial properties of the azole. Accordingly, the present compounds exterminate bacteria with both the antibacterial mechanism of the azole along with the ROS produced when the AIE unit is exposed to light. In addition, the intrinsic imagining ability of the present compounds enables them to be used as imaging tools for monitoring the drug-bacteria interaction. Collectively, the present compounds provide multiple functions including imaging, monitoring, and bacterial infection inhibition for integrated diagnosis and treatment in clinical practices.

In an embodiment, the compounds have the following backbone structural formula:

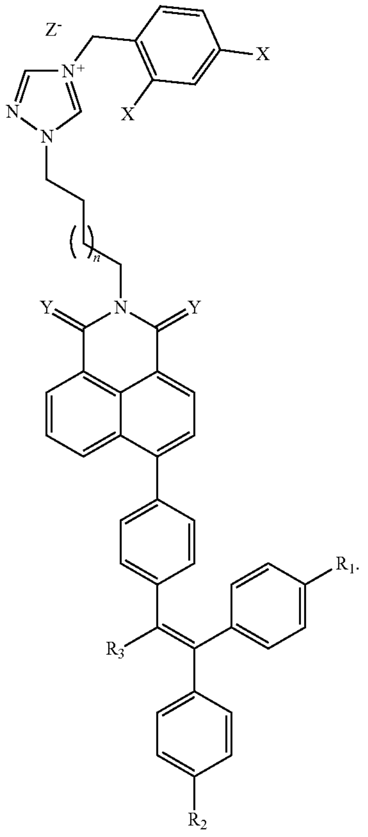

In some embodiments, the present compounds are used to treat bacterial infections and act as an imaging agent for viewing an interaction between the compound and the bacteria of an infection.

BRIEF DESCRIPTION OF DRAWINGS

Various embodiments will now be described in detail with reference to the accompanying drawings.

FIG. 15C is a graph plotting survival rate versus time of *E. coli* and MDR *E. coli*. FIG. 15D is a graph plotting survival rate versus time of *K. pneumoniae* and MDR *K. pneumoniae*. FIG. 15E is a graph plotting survival rate versus time of *S. epidermidis* and MDR *S. epidermidis*. FIG. 15F is a graph plotting survival rate versus time of *S. aureus* and MDR *S. aureus.*

FIG. 16A is a graph plotting the survival rate versus time of *E. coli*. FIG. 16B is a graph plotting the survival rate versus time of *S. epidermidis.*

FIG. 17A is a graph comparing *E. coli*, MDR *E. coli, S. epidermidis*, and MDR *S. epidermidis* survival rate versus time. FIG. 17B is a graph comparing *K. pneumoniae*, MDR *K. pneumoniae, S. epidermidis*, and MDR *S. epidermidis* survival rate versus time. FIG. 17C is a graph comparing *K. pneumoniae*, MDR *K. pneumoniae, S. aureus*, and MDR *S. aureus* survival rate versus time.

FIG. 18A shows the survival rate versus concentration of HAFs in multiple light conditions. FIG. 18B shows the survival rate versus concentration of HUVECs in multiple light conditions.

FIG. 24A shows FE-SEM images. FIG. 24B shows FEHR-TEM images with the arrows indicate the destroyed membrane. FIG. 24C shows Elemental mapping of F of *E. coli* and *S. epidermidis*. FIG. 24D is a graph plotting elemental curve measured on the super-thin slices of TriPE-NT-treated *E. coli* from the region marked by the rectangle in FIG. 24C. FIG. 24 E is a graph plotting the elemental curve measured on the super-thin slices of TriPE-NT-treated *S. epidermidis* from the region marked by rectangle in FIG. 24C.

FIG. 26A illustrates the process of establishing bacteria-infected full-thickness skin wound models on rats. FIG. 26B shows photographs of wounds treated by TriPE-NT plus white-light irradiation (4 mW cm-2) after injury for different time periods. FIG. 26C is a graph plotting the proportion of the *E. coli* and MDR *E. coli* infected wound area on day 3 and day 7 after the injury. FIG. 26D is a graph plotting the proportion of the *S. epidermidis* and MDR *S. epidermidis* infected wound area on day 3 and day 7 after the injury (each experiment was repeated at least 5 times).

DETAILED DESCRIPTION

Definitions

Figure 1:
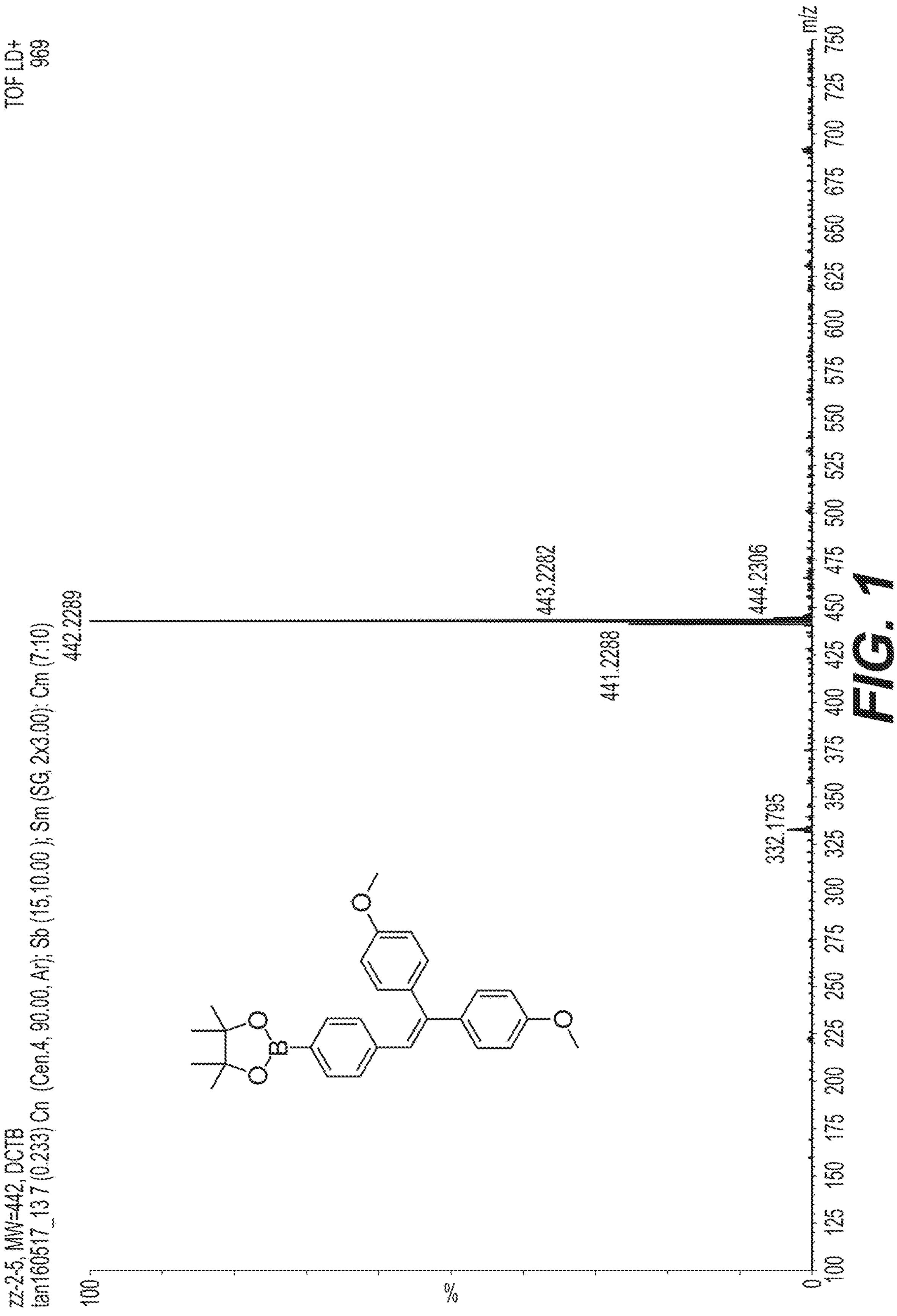
FIG. 1 is a high-resolution mass spectrum image of compound 3.
Figure 2:
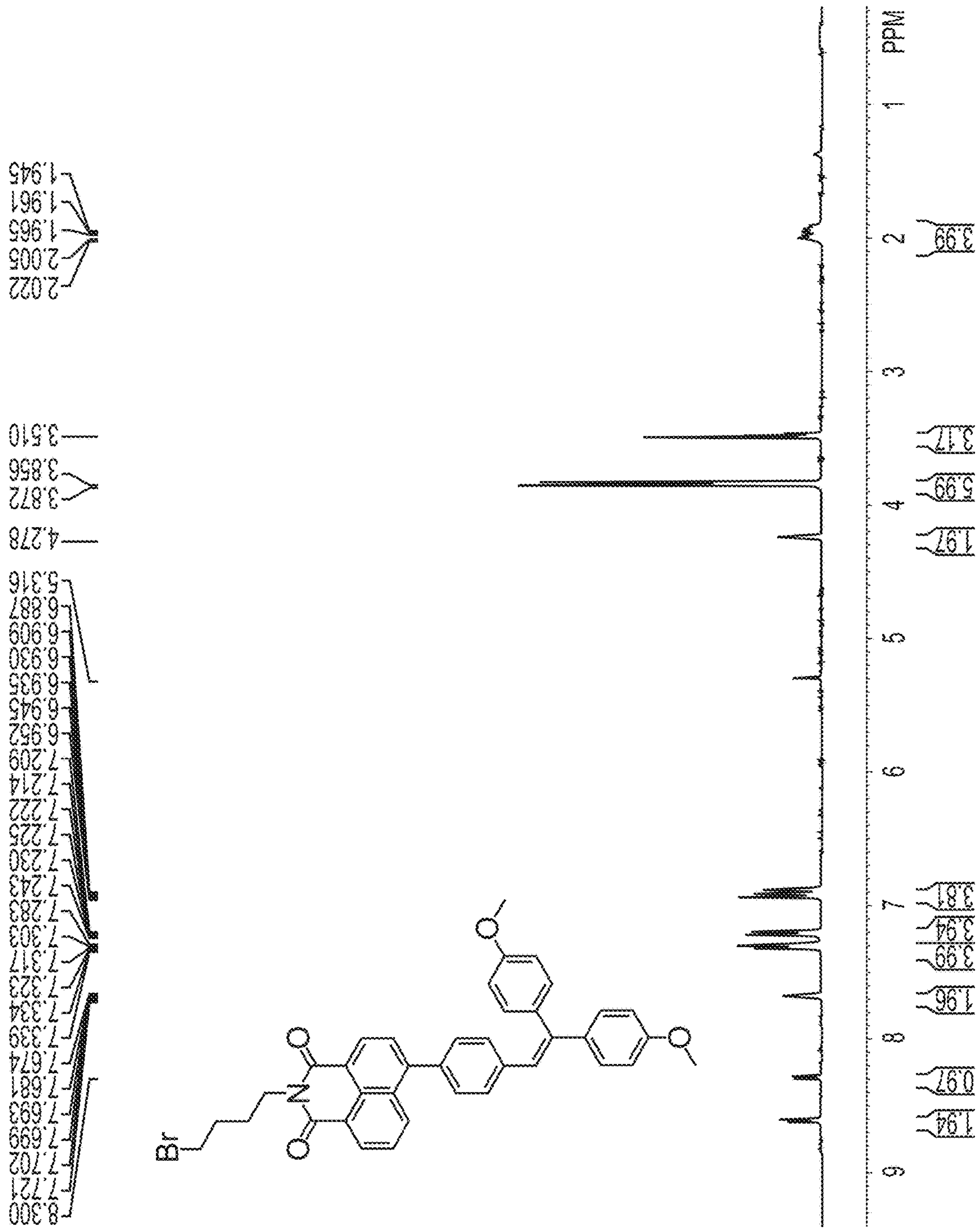
FIG. 2 is a proton magnetic resonance (H NMR) spectroscopy image of compound 2.
Figure 3:
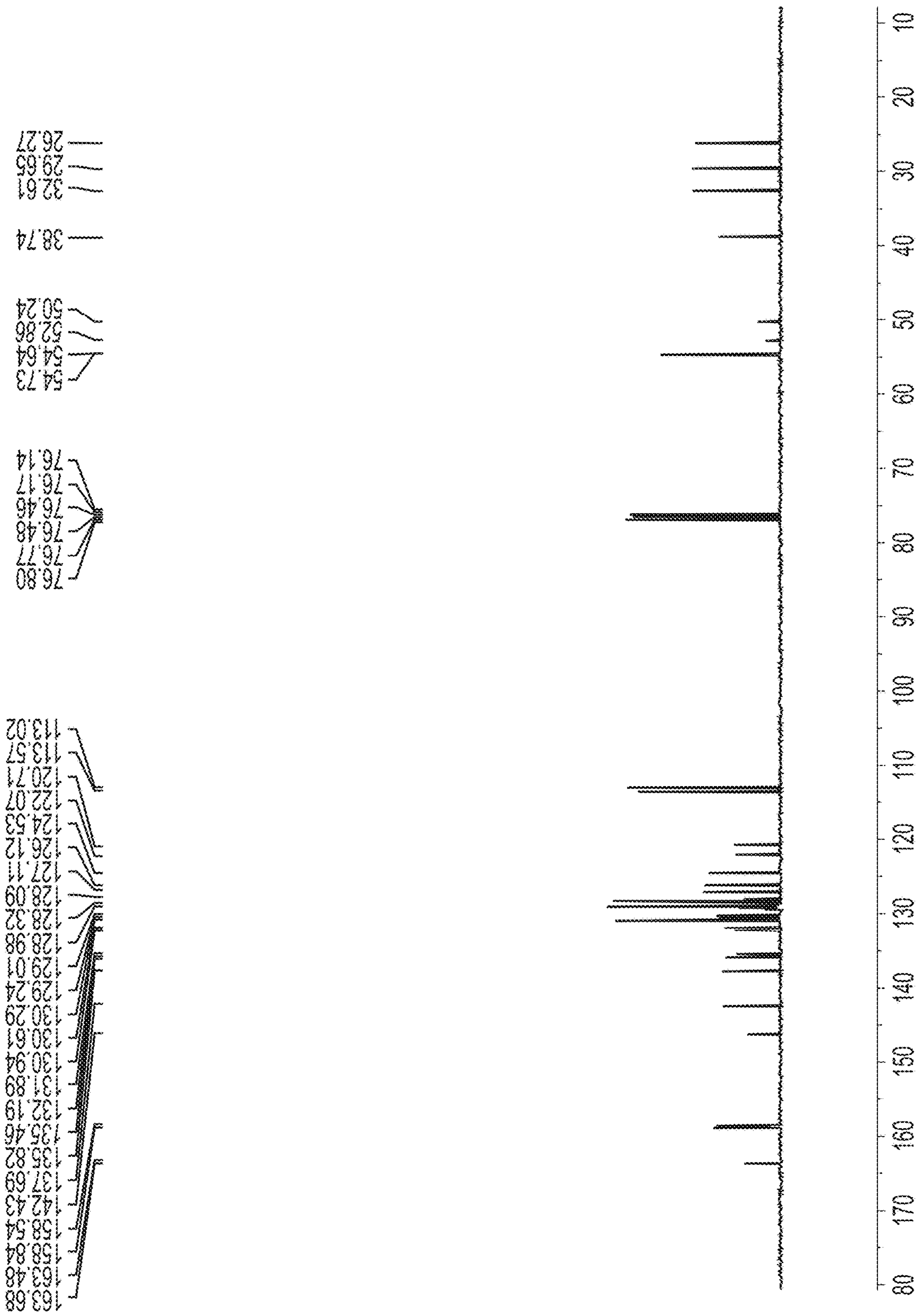
FIG. 3 is a carbon magnetic resonance (C NMR) spectroscopy image of compound 2.
Figure 4:
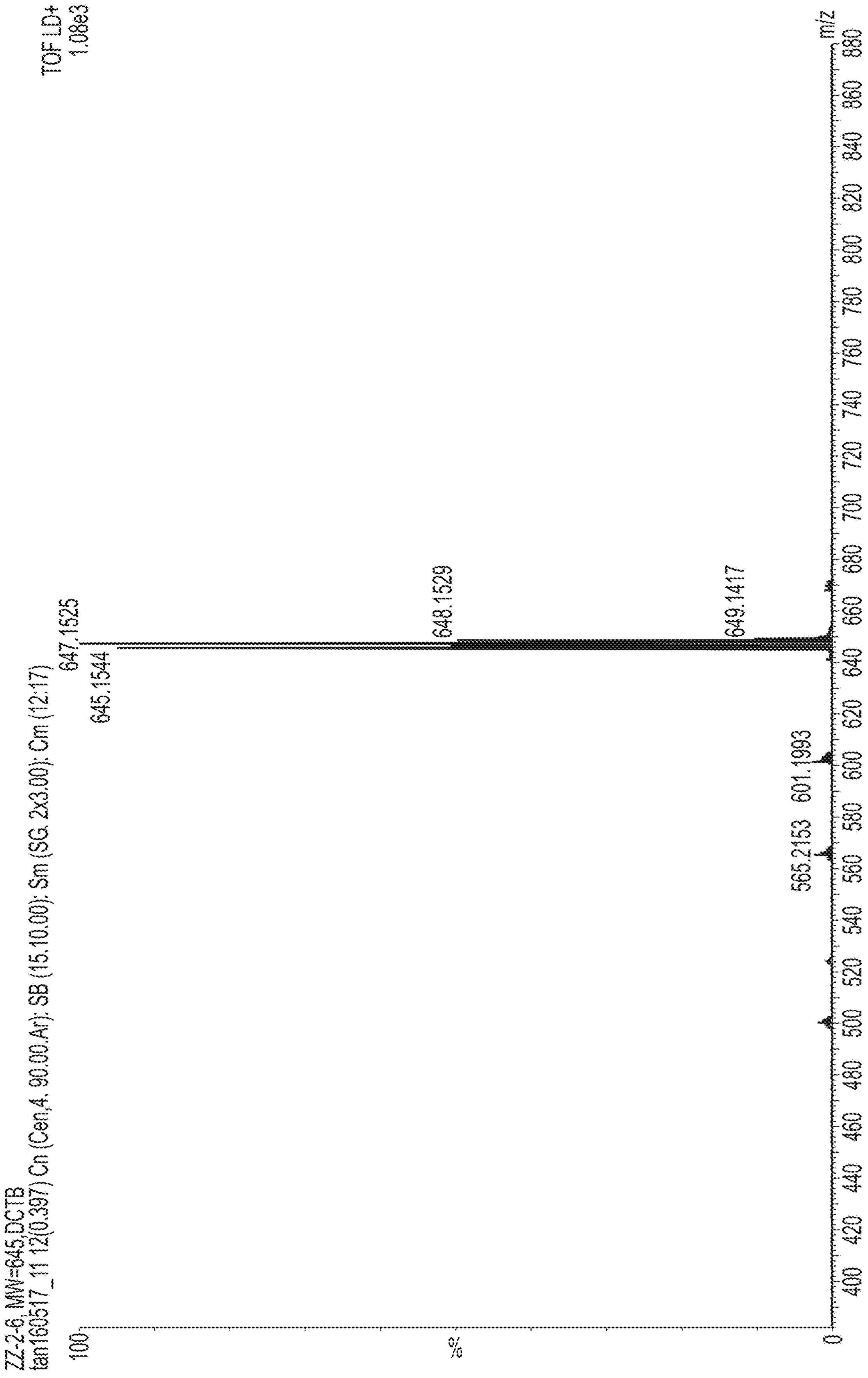
FIG. 4 is a high-resolution mass spectrum image of compound 3.
Figure 5:
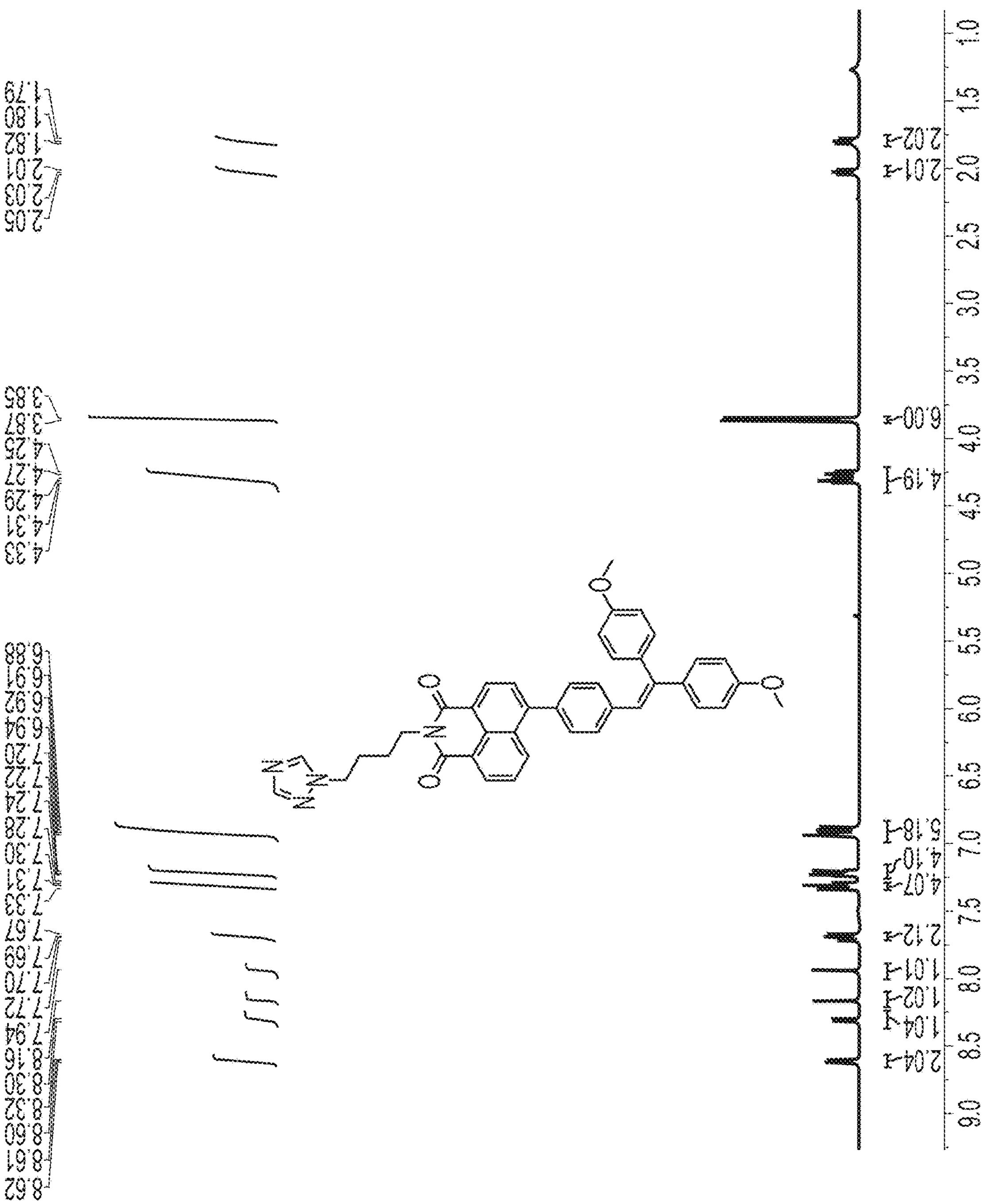
FIG. 5 is a H NMR spectroscopy image of compound 1.
Figure 6:
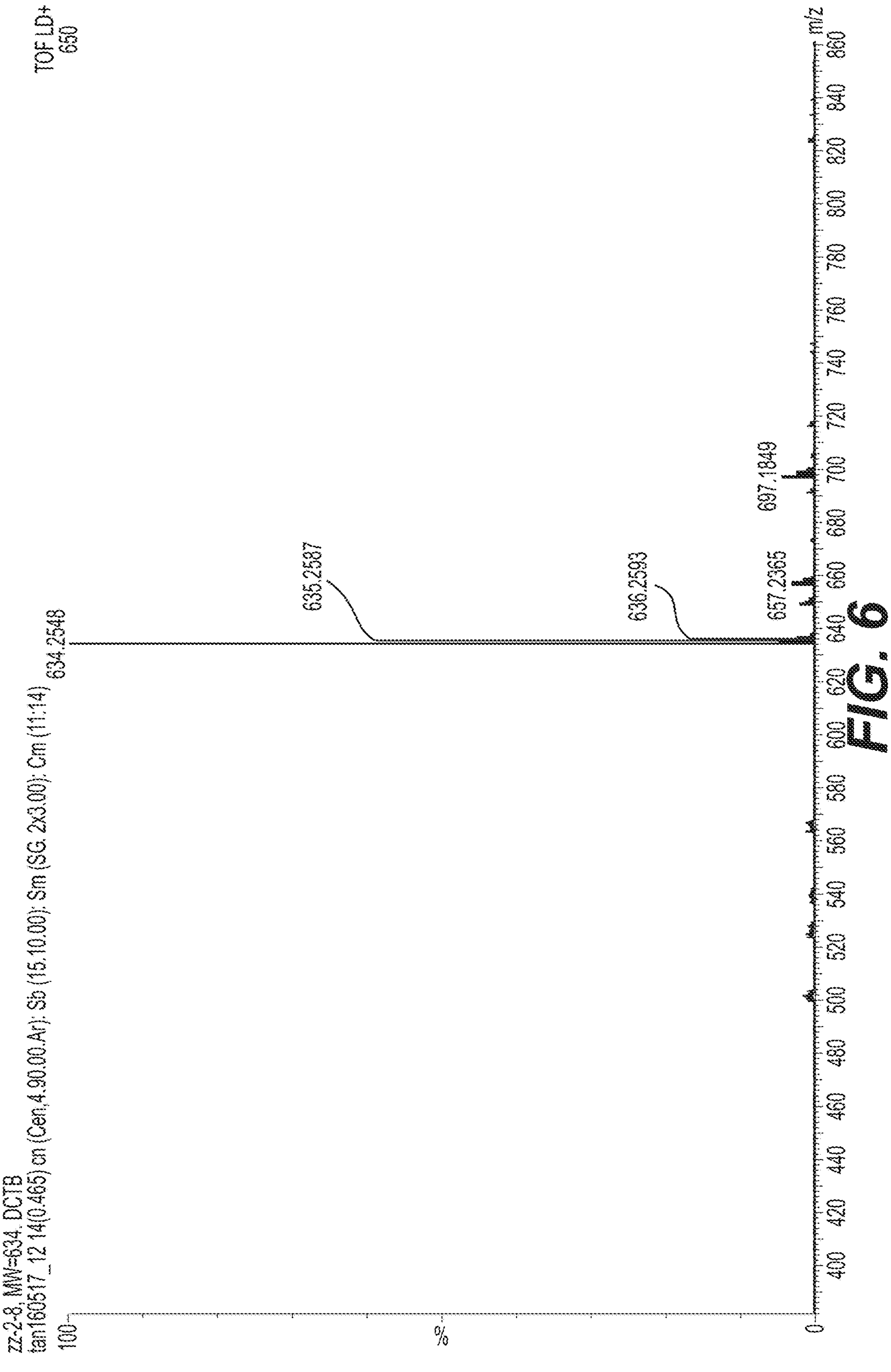
FIG. 6 is a high-resolution mass spectrum image of compound 1.
Figure 7:
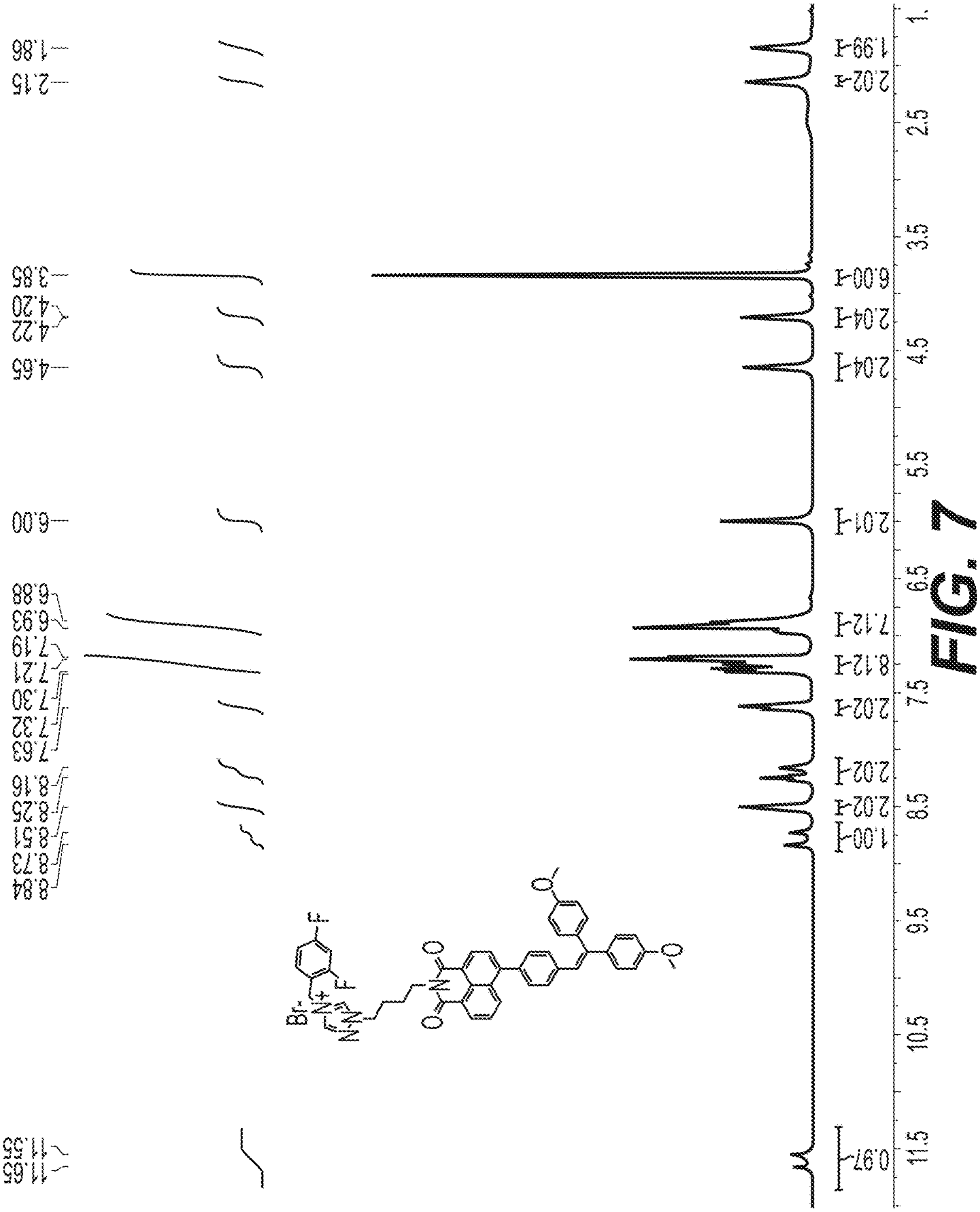
FIG. 7 is a H NMR spectroscopy image of TriPE-NT.
Figure 8:
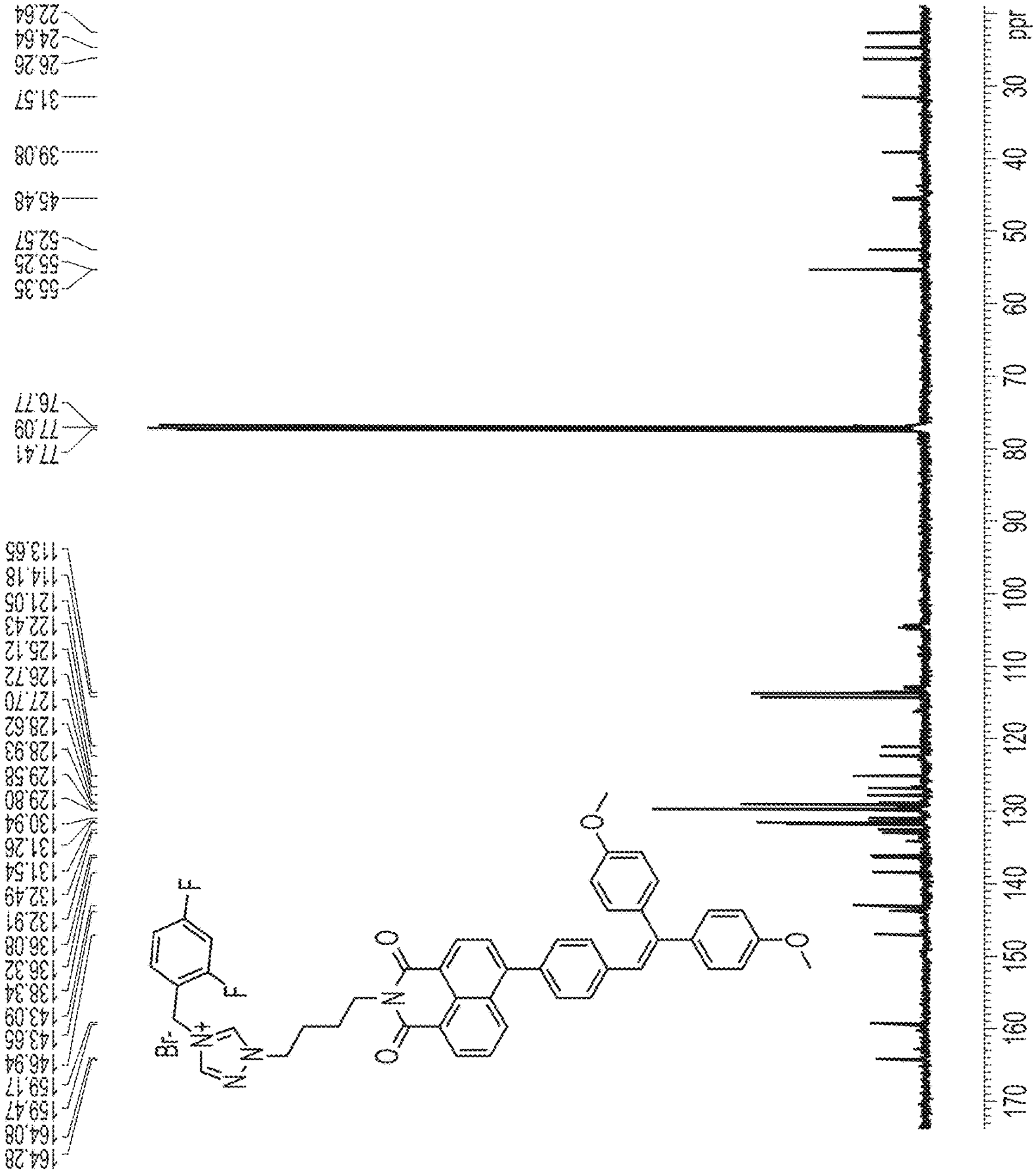
FIG. 8 is a C NMR spectroscopy image of TriPE-NT.
Figure 9:
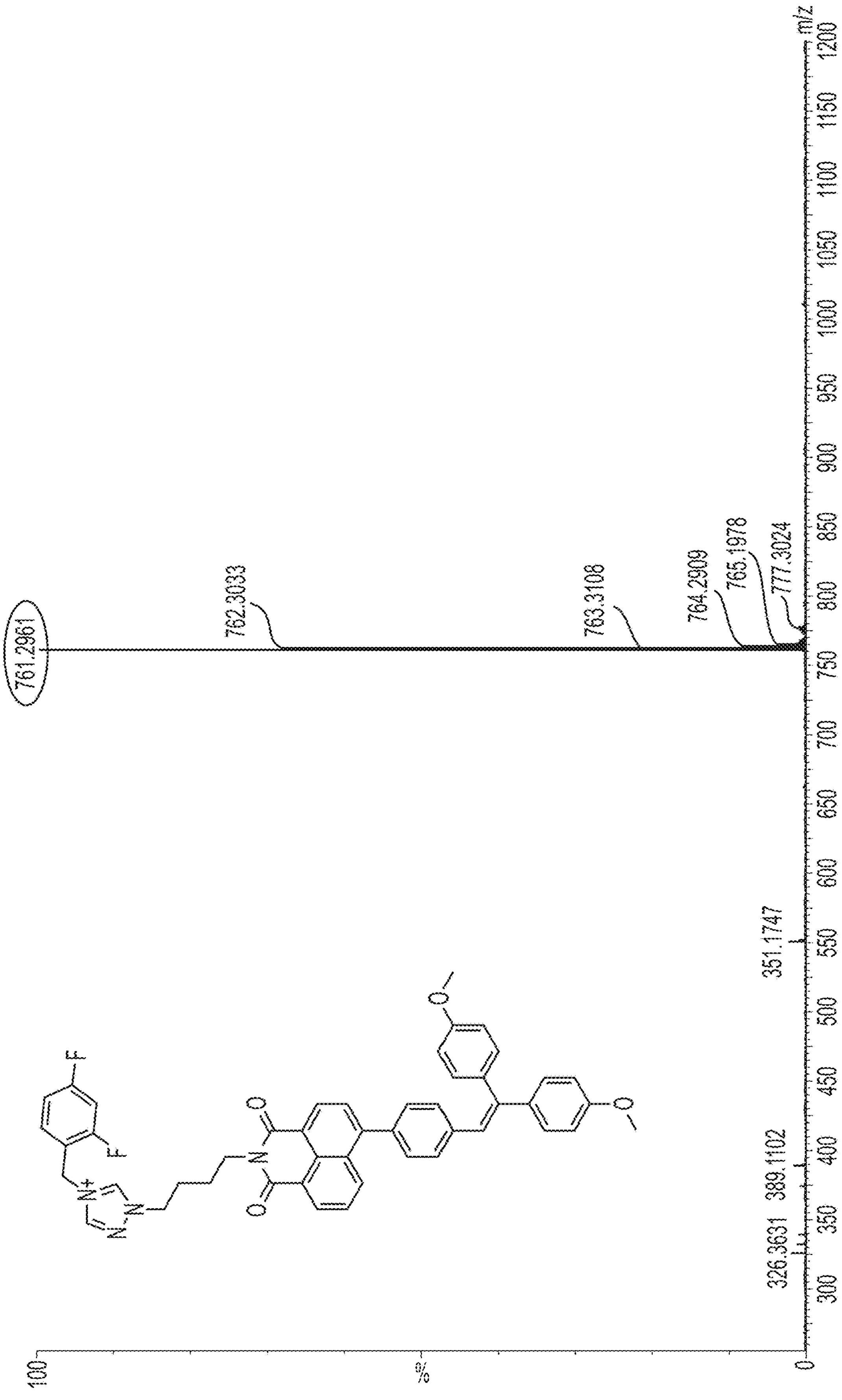
FIG. 9 a high-resolution mass spectrum image of TriPE-NT.

The following definitions are provided for the purpose of understanding the present subject matter and for constructing the appended patent claims.

It is noted that, as used in this specification and the appended claims, the singular forms "a", "an", and "the" include plural references unless the context clearly dictates otherwise.

"Agent," as used herein, refers to a chemical or biological material that can be used in a therapeutic regiment. Example agents include DNA, RNA, SiRNA, pharmaceuticals, or drugs The term "$\lambda_{ex}$" as used herein refers to excitation wavelength.

The phrase "aggregation induced emission" or "AIE" as used herein refers to the phenomenon manifested by compounds exhibiting significant enhancement of light-emission upon aggregation in the amorphous or crystalline (solid) states whereas they exhibit weak or almost no emission in dilute solutions.

As used herein, "halo" or "halogen" refers to fluoro, chloro, bromo, and iodo.

As used herein, "alkyl" refers to a straight-chain or branched saturated hydrocarbon group. Examples of alkyl groups include methyl (Me), ethyl (Et), propyl (e.g., n-propyl and z'-propyl), butyl (e.g., n-butyl, z'-butyl, sec-butyl, tert-butyl), pentyl groups (e.g., n-pentyl, z'-pentyl, -pentyl), hexyl groups, and the like. In various embodiments, an alkyl group can have 1 to 40 carbon atoms (i.e., C1-40 alkyl group), for example, 1-30 carbon atoms (i.e., C1-30 alkyl group). In some embodiments, an alkyl group can have 1 to 6 carbon atoms, and can be referred to as a "lower alkyl group". Examples of lower alkyl groups include methyl, ethyl, propyl (e.g., n-propyl and z'-propyl), and butyl groups (e.g., n-butyl, z'-butyl, sec-butyl, tert-butyl). In some embodiments, alkyl groups can be substituted as described herein. An alkyl group is generally not substituted with another alkyl group, an alkenyl group, or an alkynyl group.

The term "alkoxy" means —O-alkyl; "hydroxyalkyl" means alkyl substituted with hydroxy; "aralkyl" means alkyl substituted with an aryl group; "alkoxyalkyl" mean alkyl substituted with an alkoxy group; "alkylamine" means amine substituted with an alkyl group; "cycloalkylalkyl" means alkyl substituted with cycloalkyl; "dialkylamine" means amine substituted with two alkyl groups; "alkylcarbonyl" means —C(O)-A*, wherein A* is alkyl; "alkoxycarbonyl" means —C(O)—OA*, wherein A* is alkyl; and where alkyl is as defined above. Alkoxy is preferably $O(C_1-C_6)$alkyl and includes methoxy, ethoxy, propoxy, butoxy, pentoxy and hexoxy.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have 6 to 24 carbon atoms in its ring system (e.g., C6-24 aryl group), which can include multiple fused rings. In some embodiments, a polycyclic aryl group can have 8 to 24 carbon atoms. Any suitable ring position of the aryl group can be covalently linked to the defined chemical structure. Examples of aryl groups having only aromatic carbocyclic ring(s) include phenyl, 1-naphthyl (bicyclic), 2-naphthyl (bicyclic), anthracenyl (tricyclic), phenanthrenyl (tricyclic), pentacenyl (pentacyclic), and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like. In some embodiments, aryl groups can be substituted as described herein. In some embodiments, an aryl group can have one or more halogen substituents, and can be referred to as a "haloaryl" group. Perhaloaryl groups, i.e., aryl groups where all of the hydrogen atoms are replaced with halogen atoms (e.g., $—C_6F_5$), are included within the definition of "haloaryl". In certain embodiments, an aryl group is substituted with another aryl group and can be referred to as a biaryl group. Each of the aryl groups in the biaryl group can be substituted as disclosed herein.

As used herein, "heteroaryl" refers to an aromatic monocyclic ring system containing at least one ring heteroatom selected from oxygen (O), nitrogen (N), sulfur (S), silicon (Si), and selenium (Se) or a polycyclic ring system where at least one of the rings present in the ring system is aromatic and contains at least one ring heteroatom. Polycyclic heteroaryl groups include those having two or more heteroaryl rings fused together, as well as those having at least one monocyclic heteroaryl ring fused to one or more aromatic carbocyclic rings, non-aromatic carbocyclic rings, and/or non-aromatic cycloheteroalkyl rings. A heteroaryl group, as a whole, can have, for example, 5 to 24 ring atoms and contain 1-5 ring heteroatoms (i.e., 5-20 membered heteroaryl group). The heteroaryl group can be attached to the defined chemical structure at any heteroatom or carbon atom that results in a stable structure. Generally, heteroaryl rings do not contain O—O, S—S, or S—O bonds. However, one or more N or S atoms in a heteroaryl group can be oxidized (e.g., pyridine N-oxide thiophene S-oxide, thiophene S,S-dioxide). Examples of heteroaryl groups include, for example, the 5- or 6-membered monocyclic and 5-6 bicyclic ring systems shown below:

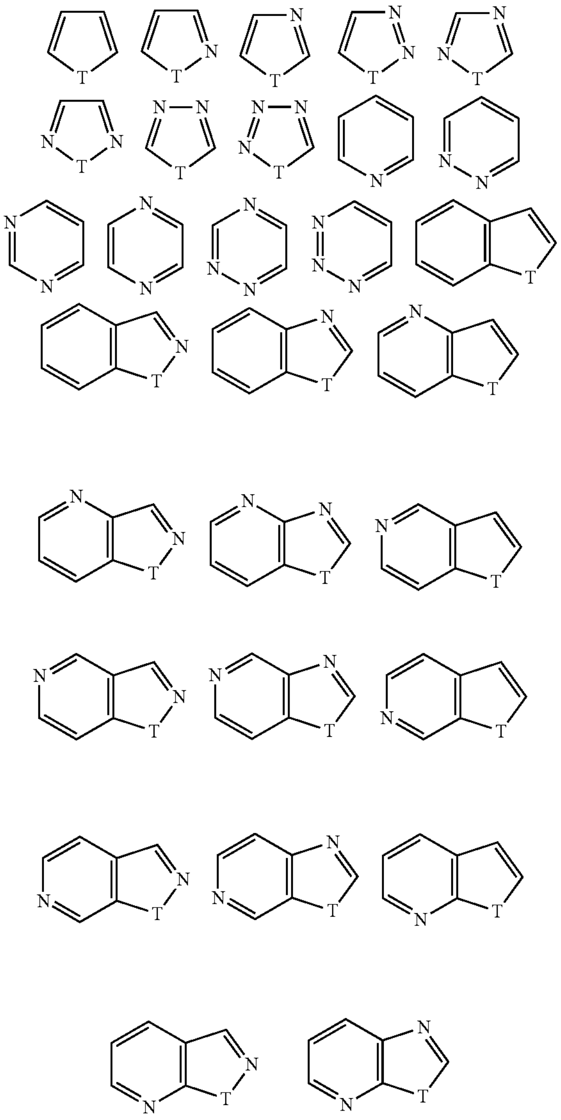

where T is O, S, NH, N-alkyl, N-aryl, N-(arylalkyl) (e.g., N-benzyl), $SiH_2$, SiH(alkyl), $Si(alkyl)_2$, SiH(arylalkyl), $Si(arylalkyl)_2$, or Si(alkyl)(arylalkyl). Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like. In some embodiments, heteroaryl groups can be substituted as described herein.

A “reactive oxygen species (ROS)” linking moiety is a moiety which can be cleaved upon exposure to a reactive oxygen species.

As used herein, “spectroscopy” encompasses any method by which matter reacts with radiated energy. This includes, but is in no way limited to, microscopy, fluorescence microscopy, UV/Vis spectrometry, and flow cytometry. A “microplate reader” as used herein, means a laboratory instrument that measures, for example, fluorescence, absorbance and luminescence of samples contained in a microplate.

As used herein, the term “incubation” or alternately, “incubating” a sample means mixing a sample. Alternately, incubating means mixing and heating a sample. “Mixing” can comprise mixing by diffusion, or alternately by agitation of a sample Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use “comprising” language. However, it will be understood by one of skill in the art, that in some specific instances, an embodiment can alternatively be described using the language “consisting essentially of” or “consisting of”.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term “about”. Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

Antibacterial Compound

In some non-limiting embodiments, the present subject matter is directed to certain antibiotic compounds having antibiotic AIE characteristics. These compounds are thus capable of staining and killing Gram-positive and/or Gram negative bacteria.

In one embodiment, the present compounds may have the following backbone structural formula:

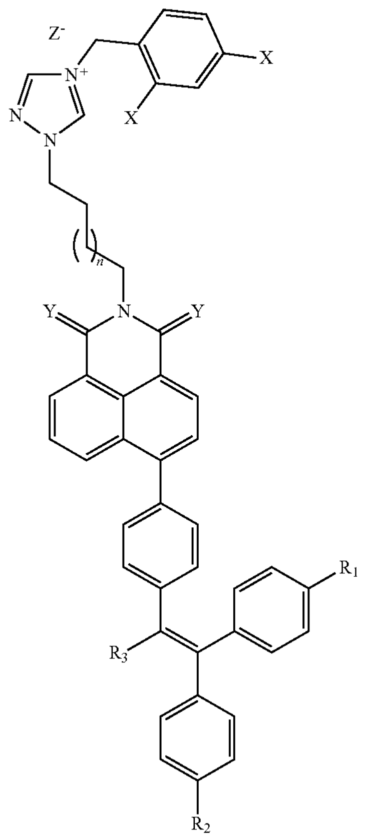

wherein n is an integer from 1 to 10; each X independently may be a halogen selected from the group consisting of F, Cl, Br, and I; each Y independently may be one of oxygen and sulfur; the counterion $Z^-$ is selected from the group consisting of $F^-$, $Cl^-$, $Br^-$, $I^-$, $At^-$, $Ts^-$, $PF_6^-$, $BF_4^-$, $SbF_6^-$, $SbF_5^-$, $CH_3COO^-$, $CF_3COO^-$, $CO_3^{2-}$, $SO_4^{2-}$, $SO_3^{2-}$, $CF_3SO_2^-$, $TsO^-$, $ClO_4^-$, $(F_3CSO_2)N^-$, and $PO_4^{3-}$; R1 and R2 may independently be selected from the group consisting of an alkyl, alkoxy, OH, $NH_2$, alkyl substituted with a hydroxy, and a 5, 6, or 7-membered nitrogen-containing unsaturated heteroaryl; and R3 may be present or absent, wherein when R3 is present, R3 may be selected from the group consisting of H, Phenyl, and CN, and when R3 is absent there is a double bond along the carbon bond having the dotted line. In addition, other suitable counterions known to one of ordinary skill in the art may further be used for the $Z^-$ counterion herein.

In some embodiments of the present antibacterial compound, each X is fluorine.

In some embodiments of the present antibacterial compound, each Y is oxygen.

In some embodiments of the present antibacterial compound, R1 is methoxy.

In some embodiments of the present antibacterial compound, R2 is methoxy.

In some embodiments of the present antibacterial compound, $Z^-$ is $Br^-$.

An embodiment of the present antibacterial compound is:

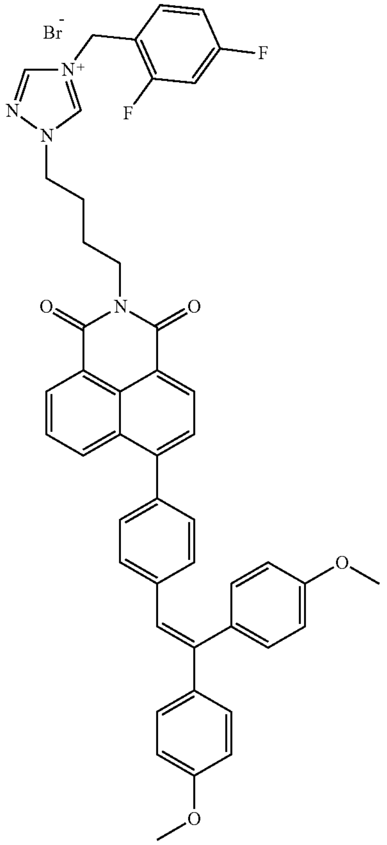

In some cases, the compound may be combined with a pharmaceutically acceptable carrier. For example, when intended for topical application, a topical carrier may be used. Well-known carriers used to formulate other topical therapeutic compositions for administration to humans will be useful with the present compound. Examples of these components that are well known to those of skill in the art are described in The Merck Index, Thirteenth Edition, Budavari et al., Eds., Merck & Co., Inc., Rahway, N.J. (2001); the CTFA (Cosmetic, Toiletry, and Fragrance Association) International Cosmetic Ingredient Dictionary and Handbook, Tenth Edition (2004); and the "Inactive Ingredient Guide", U.S. Food and Drug Administration (FDA) Center for Drug Evaluation and Research (CDER) Office of Management, January 1996, the contents of which are hereby incorporated by reference in their entirety. Examples of such useful pharmaceutically acceptable excipients, carriers and diluents include purified water, physiological saline, Ringer's solution, dextrose solution, Hank's solution, and DMSO, which are among those preferred for use herein.

These additional other inactive components, as well as effective formulations and administration procedures, are well known in the art and are described in standard textbooks, such as Goodman and Gillman's: The Pharmacological Bases of Therapeutics, 8th Ed., Gilman et al. Eds. Pergamon Press (1990) and Remington's Pharmaceutical Sciences, 17th Ed., Mack Publishing Co., Easton, Pa. (1990), both of which are incorporated by reference herein in their entirety.

Some embodiments of the present subject matter include a method of treating a bacterial infection in a patient, comprising: administering the present antibacterial compound to a site of an infection in a patient and illuminating the site of the infection to generate reactive oxygen species from the present antibacterial compound. The site of the infection may be illuminated with white light for a duration of time in the range of 2 minutes to 30 minutes.

Some embodiments of the present subject matter include a method of generating reactive oxygen species, comprising: administering the present antibacterial compound to a portion of an object and illuminating the portion of the object. The portion of the object may be illuminated with white light for a duration of time in the range of 2 minutes to 30 minutes.

Some embodiments of the present subject matter include a method of imaging antibiotic interaction with bacteria, comprising: administering the present antibacterial compound to a bacterial infection; and imaging the bacterial infection to view fluorescence produced from aggregation of the present antibacterial compound.

EXAMPLES

Materials and Characterization

Compound 4 was from AIEgen Biotech Co., Ltd. All other chemicals and solvents were from Sigma-Aldrich or Acros. Tetrahydrofuran (THF) was dried by distillation using sodium as drying agent. Phosphate buffer saline (PBS) was from Sigma-Aldrich. Propidium iodide (PI) was from DoJinDo. *E. coli, K. pneumoniae, S. epidermidis* and *S. aureus* were from ATCC. MDR *E. coli*, MDR *K. pneumoniae*, MDR *S. epidermidis* and MDR *S. aureus* were from Beijing Tiantan Hospital (China), Milli-Q water was from a Milli-Q purification system (Merck Millipore, Germany). NMR spectra were measured on a Bruker ARX 400 NMR spectrometer using tetramethylsilane (TMS; δ=0) as internal reference. High-resolution mass spectrometry (HR-MS) was obtained on a Finnigan MAT TSQ 7000 Mass Spectrometer System operated in a MALDI-TOF mode. UV-vis spectra were measured on a Milton Roy Spectronic 3000 Array spectrophotometer. Dynamic light scattering (DLS) was performed on a ZetaPlus (Brookhaven Instruments Corporation). Steady-state photoluminescence (PL) spectra were measured on a Perkin-Elmer spectrofluorometer LS 55.

Example 1

Synthesis 4,4'-dimethoxytriphenylethylene-4,4,5,5-tetramethyl-1,3,2-dioxaborolane (Compound 3) and 6-bromo-2-(4-bromobutyl)-naphthalenediimide were synthesized according to known methods. The synthetic route for TriPE-NT is shown in Scheme S1 below:

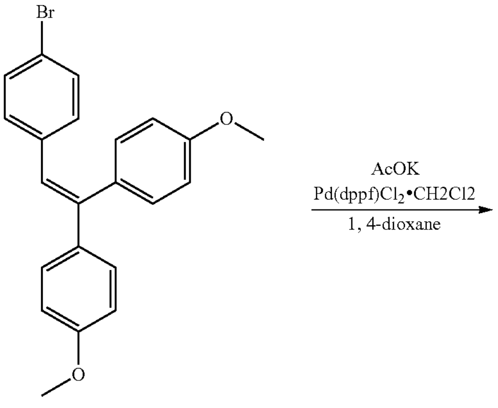

4

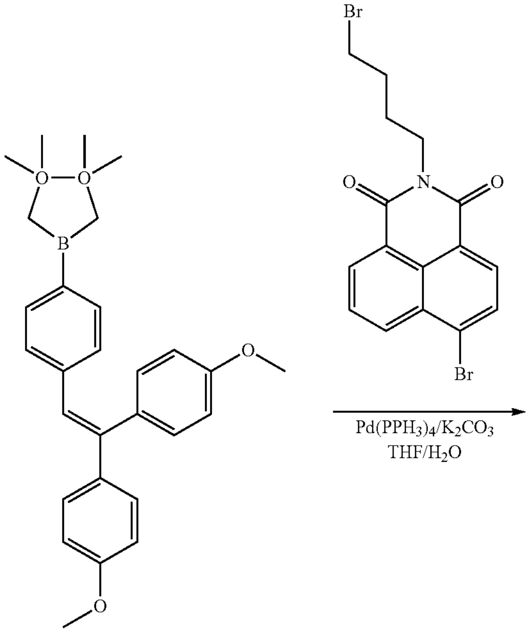

3

-continued

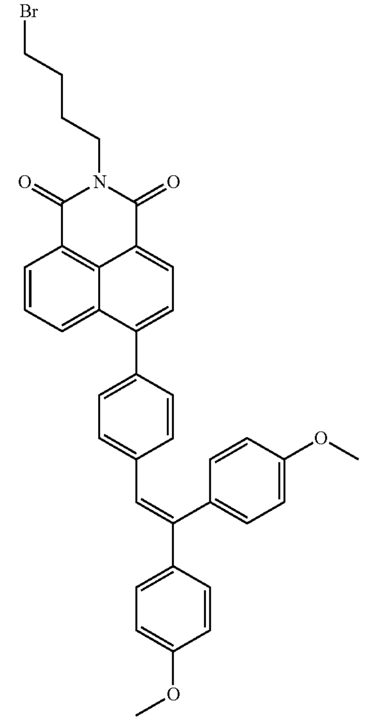

2

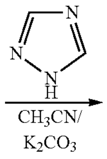

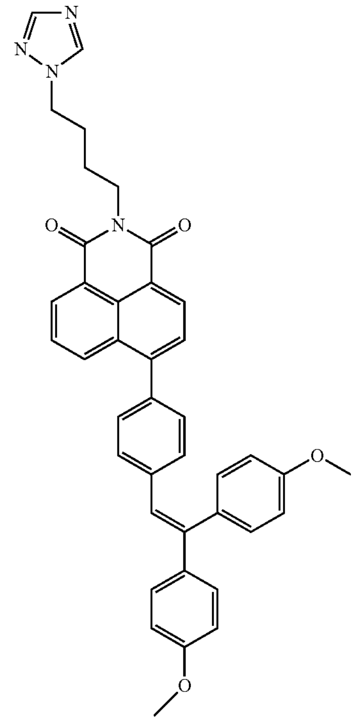

1

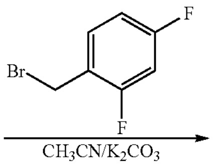

-continued

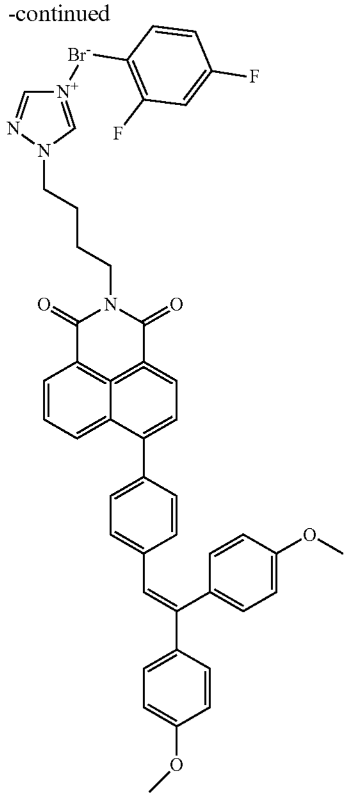

TriPE-NT

S1

Figure 10:
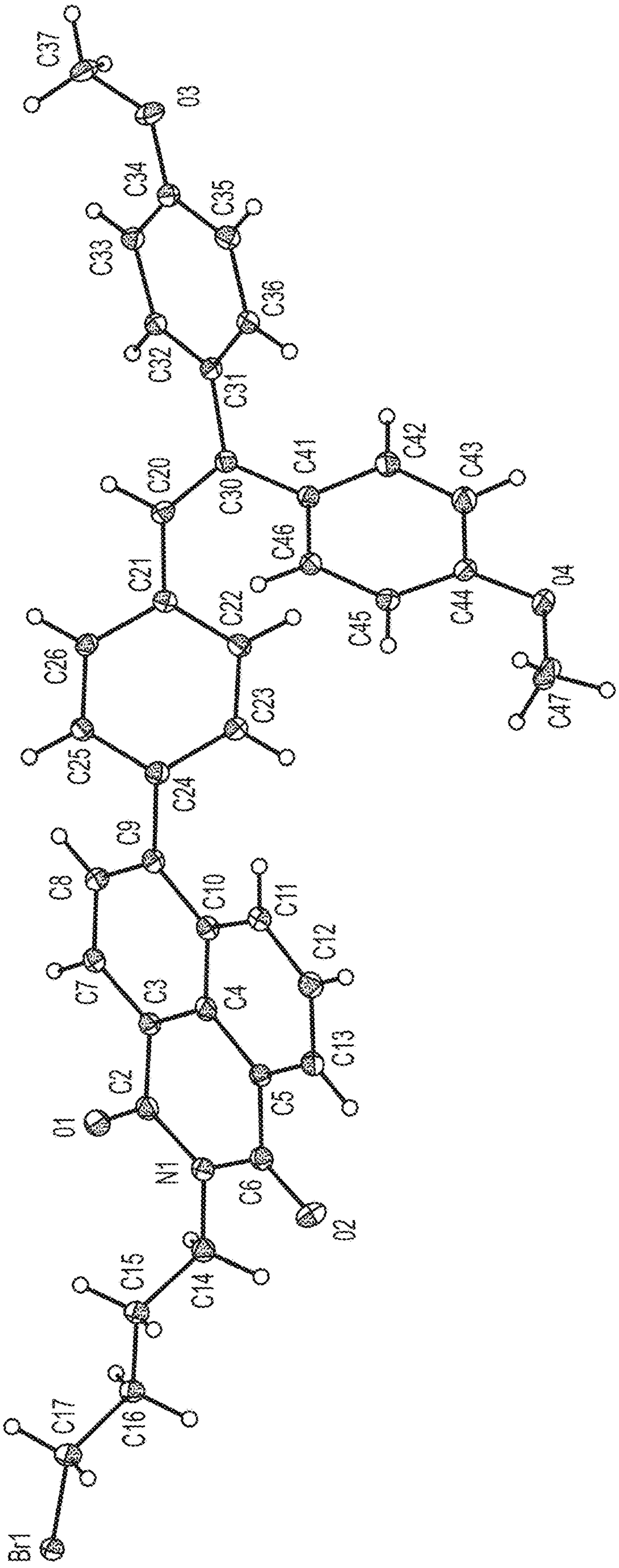
FIG. 10 is diagram depicting the single crystal structure of compound 2.

Compound 3 and 6-bromo-2-(4-bromobutyl)-naphthalimide were synthesized according to known methods. Suzuki coupling of compound 3 and 6-bromo-2-(4-bromobutyl)-naphthalimide yielded compound 2 in a moderate yield. The $S_N2$ reaction between compound 2 and triazole yielded compound 1 efficiently. Finally, TriPE-NT was readily prepared by $S_N2$ reaction between compound 1 and 1-(bromomethyl)-2,4-difluorobenzene in a yield of 52%. TriPE-NT and all the intermediate products were fully characterized by nuclear magnetic resonance spectroscopy ($^1H$ NMR, $^{13}C$ NMR) and high-resolution mass spectroscopy (HRMS) with satisfactory results (Figures. 1-9). The single crystal of intermediate 2 was obtained, which further confirmed the structure of TriPE-NT (FIG. 10).

Synthesis of Compound 2

Compound 3 (210 mg, 0.47 mmol), 6-bromo-2-(4-bromobutyl)-naphthalenediimide (150 mg, 0.36 mmol), $Pd(PPh_3)_4$ (116 mg, 28%) and $K_2CO_3$ (497 mg, 3.6 mmol) were dissolved in a mixture of distilled THF (15 mL) and deoxygenated $H_2O$ (6 mL) under nitrogen. The mixture was then stirred at 80° C. for 48 h. After cooling to room temperature, the mixture was washed with water twice and extracted with dichloromethane. After solvent evaporation, the crude product was purified by silica-gel chromatography using chloroform as eluent and recrystallization, affording 140 mg of 2. Yield: 60%. $^1H$ NMR (400 MHz, $CDCl_3$, 25° C.), δ (ppm): 8.61-8.58 (m, 2H), 8.30-8.28 (d, J=8 Hz, 1H), 7.70-7.65 (m, 2H), 7.32-7.28 (m, 4H), 7.23-7.19 (m, 4H), 6.94-6.87 (m, 5H) 4.25-4.22 (m, 2H), 3.86 (s, 3H), 3.83 (s, 3H), 3.50-3.47 (m, 3H), 2.03-1.91 (m, 4H). $^{13}C$ NMR (100 MHz, $CDCl_3$, 25° C.), δ (ppm): 163.7, 163.5, 158.8, 158.5, 146.2, 142.4, 137.7, 135.8, 135.5, 132.2, 131.9, 130.9, 130.6, 130.3, 129.2, 129.0, 128.3, 128.1, 127.1, 126.1, 124.5, 122.1, 120.7, 113.6, 113.0, 54.6, 50.2, 38.7, 32.6, 29.7, 26.3. HRMS (MALDI-TOF): m/z: $[M]^+$ calculated for $C_{38}H_{32}BrNO_4$, 645.1515; found, 645.1544.

Synthesis of Compound 1

Compound 2 (65 mg, 0.1 mmol), 1,2,4-triazole (10 mg, 0.14 mmol), $K_2CO_3$ (21 mg, 0.15 mmol) and TBAB (5 mg) were dissolved in $CH_3CN$ (5 mL) and stirred at 60° C. under nitrogen. After 1 h, a large amount of yellow pellet was precipitated and collected. The crude product was purified by silica-gel chromatography using DCM/$CH_3OH$=4/1 as eluent, affording 32 mg of 1. Yield: 50%. $^1H$ NMR (400 MHz, $CDCl_3$, 25° C.), δ (ppm): 8.62-8.60 (t, d=4 Hz, 2H), 8.32-8.30 (d, J=8 Hz, 1H), 8.16 (s, 1H), 7.94 (s, 1H), 7.72-7.67 (m, 2H), 7.33-7.30 (m, 4H), 7.24-7.20 (m, 4H), 6.94-6.88 (m, 5H) 4.33-4.25 (m, 4H), 3.87 (s, 3H), 3.83 (s, 3H), 3.50-3.47 (m, 3H), 2.05-2.01 (m, 2H), 1.82-1.79 (m, 2H). HRMS (MALDI-TOF): m/z: $[M]^+$ calcd for $C_{40}H_{34}N_4O_4$, 634.2580; found, 634.2538.

Synthesis of Compound TriPE-NT

Compound 1 (63 mg, 0.1 mmol) and 1-(bromomethyl)-2,4-difluorobenzene (31 mg, 0.15 mmol) dissolved in $CH_3CN$ (5 mL) were stirred in $CH_3CN$ at 80° C. under nitrogen for 5 h. The mixture was cooled to room temperature and the solvent was removed under reduced pressure. The crude product was recrystallized with ether and DCM twice, affording 36 mg of TriPE-NT. Yield: 43%. $^1H$ NMR (400 MHz, $CDCl_3$, 25° C.), δ (ppm): 11.65-11.55 (t, d=4 Hz, 2H), 8.84-8.73 (m, 1H), 8.51 (br, 2H), 8.25-8.16 (m, 2H), 7.63 (br, 2H), 7.32-7.19 (m, 8H), 6.93-6.88 (m, 7H) 6.00 (s, 2H), 4.65 (s, 2H), 4.22-4.20 (s, 2H), 3.85 (s, 6H), 2.15 (br, 2H), 1.86 (br, 2H). $^{13}C$ NMR (100 MHz, $CDCl_3$, 25° C.), δ (ppm): 164.3, 164.1, 159.5, 159.2, 146.9, 143.7, 143.1, 138.3, 136.3, 136.1, 132.9, 132.5, 131.5, 131.3, 130.9, 129.8, 129.6, 128.9, 128.6, 127.7, 126.7, 125.1, 122.4, 121.1, 114.1, 113.7, 55.4, 55.3, 52.6, 45.5, 39.1, 31.6, 26.3, 24.6, 22.6. HRMS (MALDI-TOF): m/z: $[M]^+$ calcd for $C_{47}H_{39}F_2N_4O_4$, 761.2934; found, 761.2951.

Example 2

Characterization of TriPE-NT

Figure 11A:
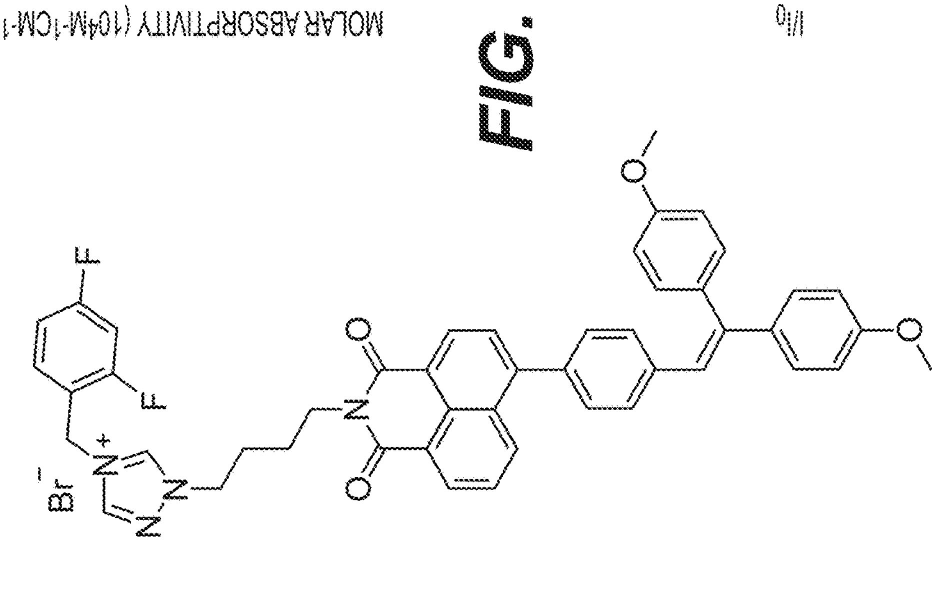
FIG. 11A is a diagram depicting the molecular structure of TriPE-NT.
Figure 11B:
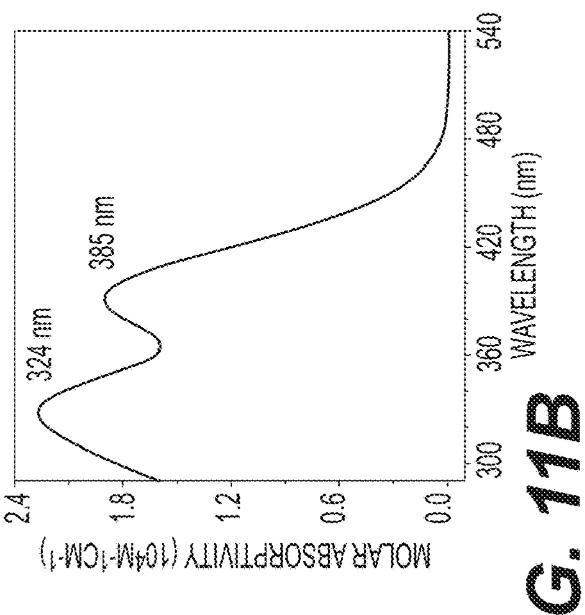
FIG. 11B is a graph plotting the UV-vis absorption spectrum of the aqueous solution of TriPE-NT.
Figure 11C:
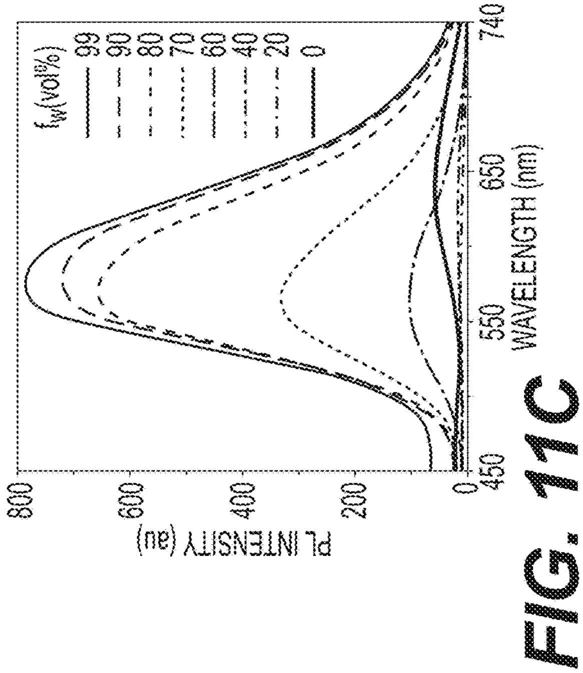
FIG. 11C is a graph plotting the PL spectra of TriPE-NT in THF/water mixtures with different water fractions ($f_w$) with a concentration of 10 μM and excitation wavelength: 385 nm.
Figure 11D:
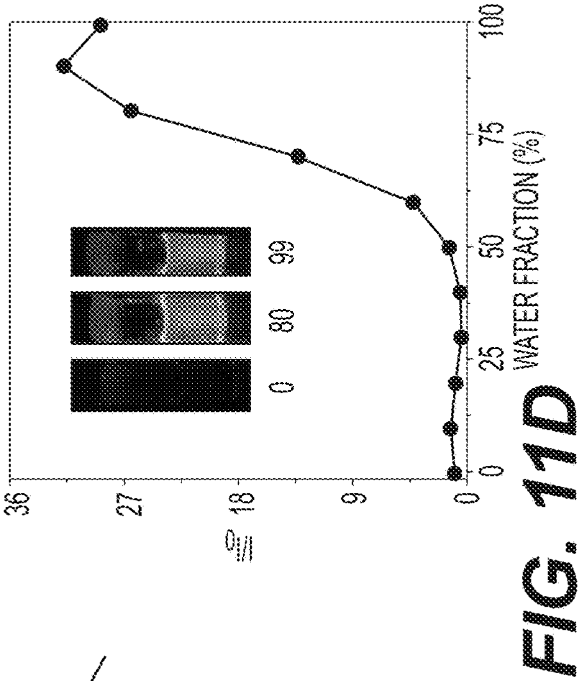
FIG. 11D is a graph plotting of relative PL ($I/I_o$) intensity versus the composition of the THF/water mixture for dissolving TriPE-NT including images of TriPE-NT in THF/water mixtures with water fraction of 0%, 80%, and 99% under 365 nm UV irradiation.
Figure 11E:
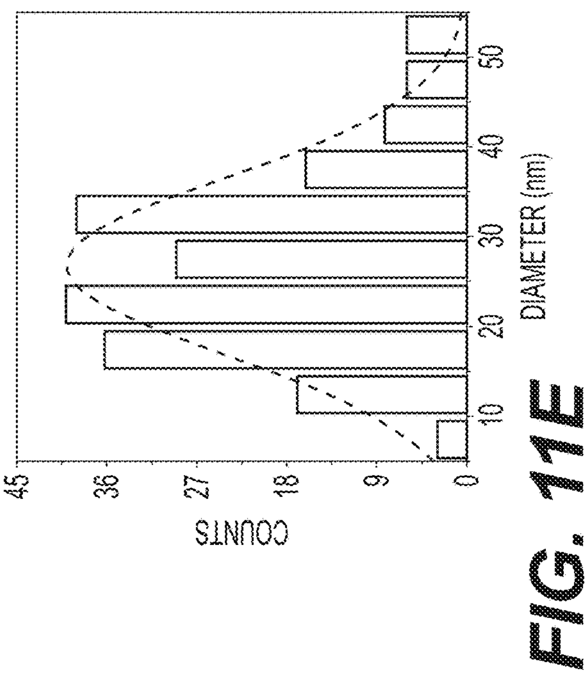
FIG. 11E is a graph plotting size distribution of the TriPE-NT aggregates calculated from scanning electron microscope (SEM) data.
Figure 12A:
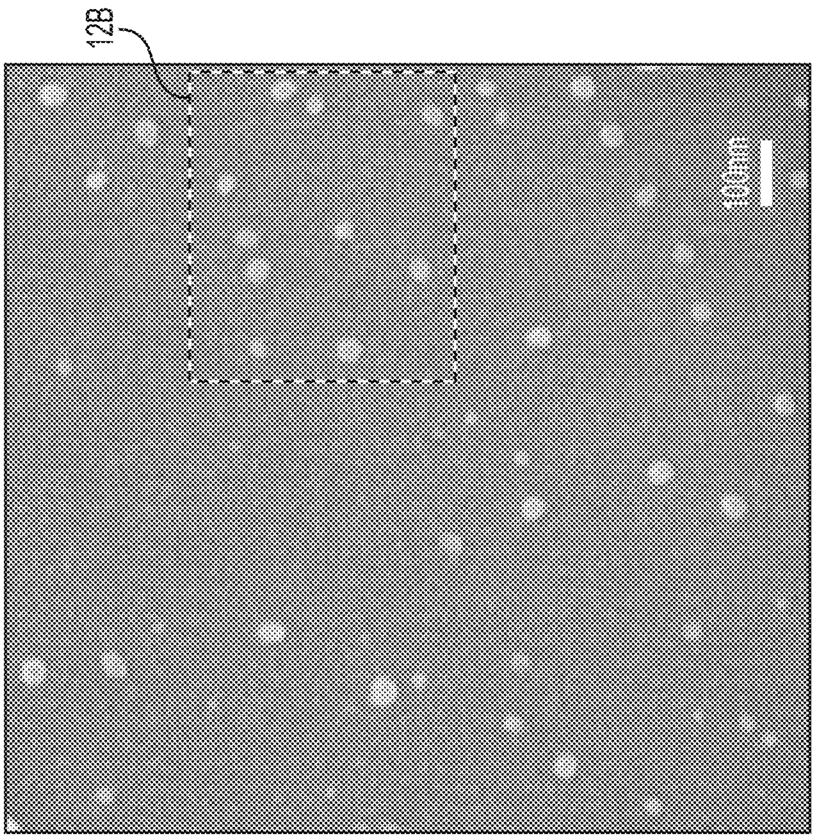
FIG. 12A is a Field Emission Scanning Electron Microscope (FE-SEM) image the nanoaggregates of TriPE-NT.
Figure 12B:
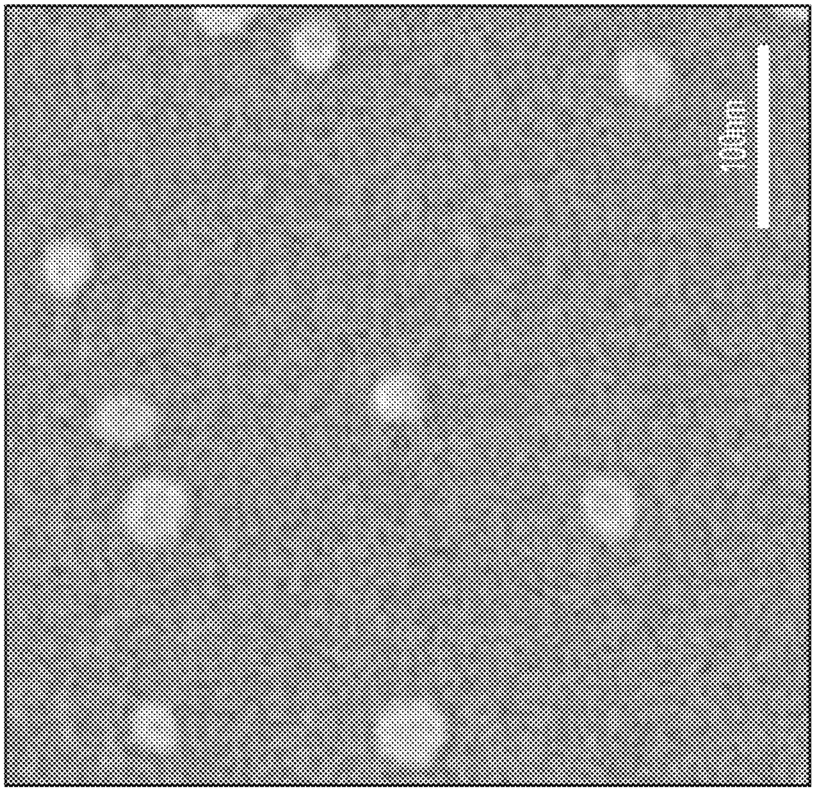
FIG. 12B is a zoomed in image of the squared off area of FIG. 12A.
Figure 13:
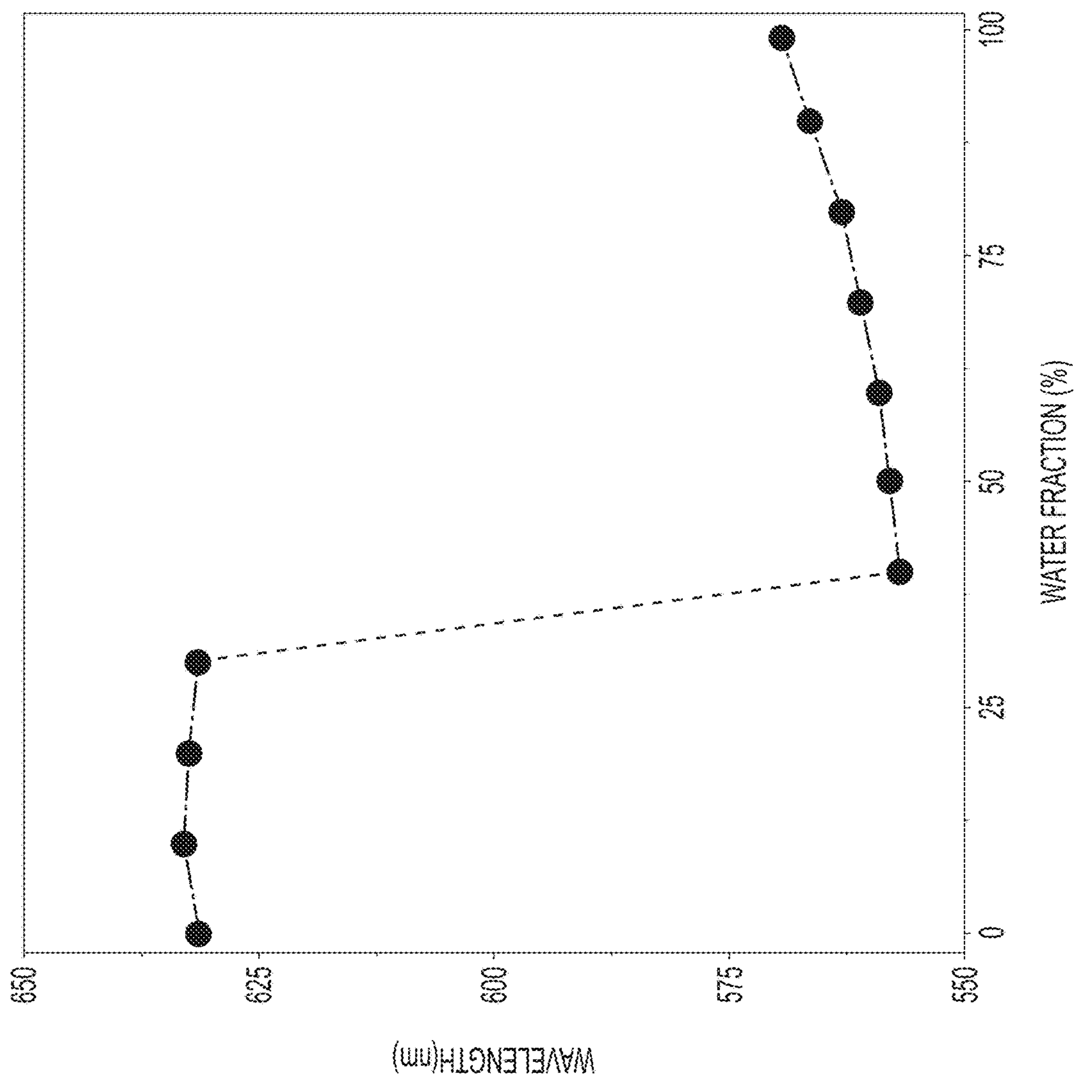
FIG. 13 is a graph plotting emission maximum versus the composition of the Tetrahydrofuran (THF)/water mixtures for TriPE-NT.
Figure 14:
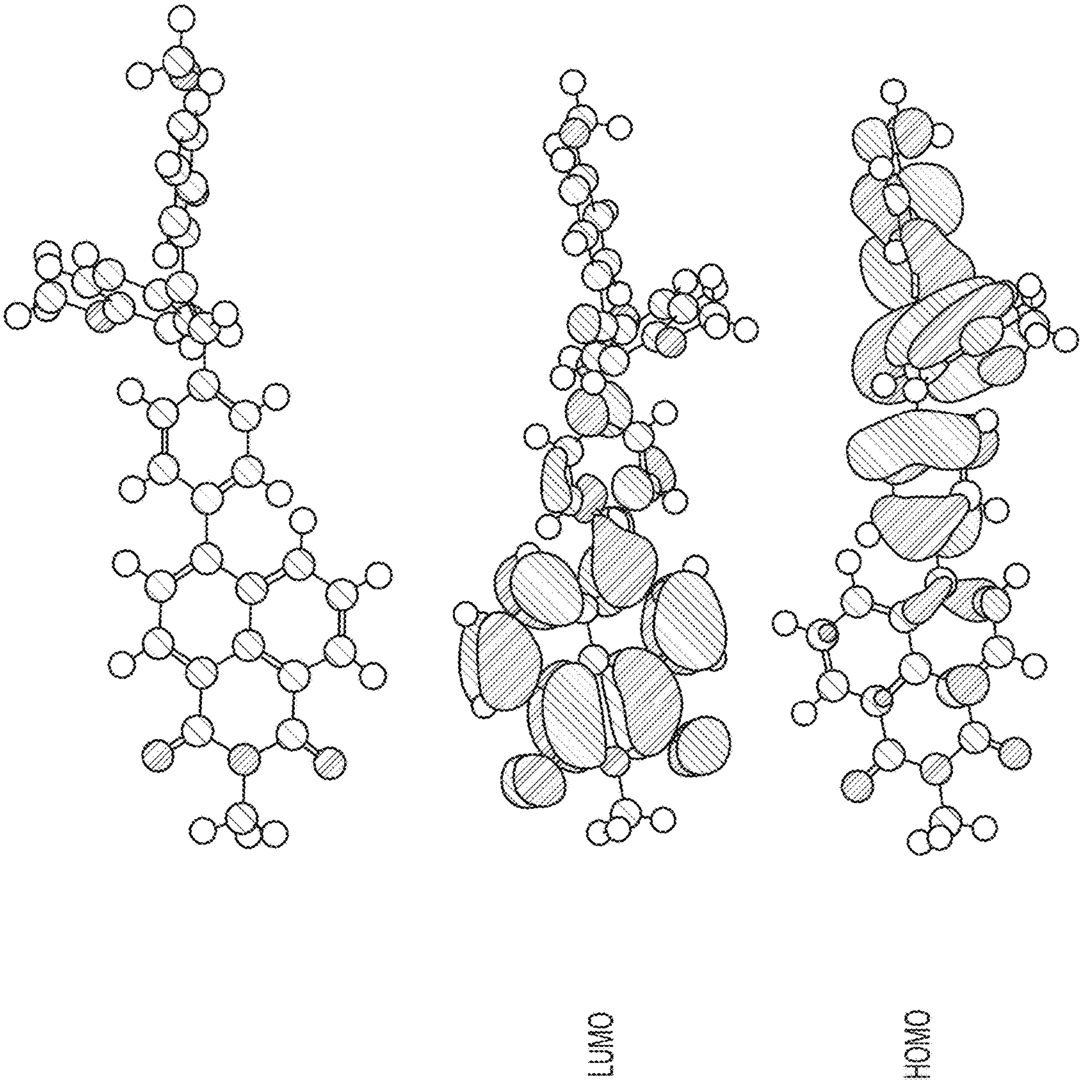
FIG. 14 shows diagrams of the optimized core structure of TriPE-NT alongside diagrams of the core structure showing electron density distribution of the highest occupied electric orbital, (HOMO) and lowest occupied electric orbital, (LUMO).

The optical properties of TriPE-NT were investigated by UV-vis and photoluminescence (PL) spectra. TriPE-NT exhibited two absorption peaks at 324 and 385 nm, which should be ascribed to the π-π* transition and intramolecular charge transfer (ICT) absorption from the TriPE moiety to the naphthalene diimides (NDI) segment. The molar absorptivity of the wavelength at 385 nm was as high as 20000 (FIG. 11B), demonstrating its good conjugation and strong absorption. TriPE-NT is non-emissive in tetrahydrofuran (THF) but brightly emissive in a solid state, its AIE characteristic were investigated by adding water to its THF solution. With the water fraction increasing from 0% to 60%, TriPE-NT showed a low PL intensity but a long emission wavelength at about 630 nm. However, when the water fraction rose to above 60%, the PL intensity of TriPE-NT intensified significantly and reached the maximum value at a water fraction of 90%, with the emission wavelength blue-shifting to about 570 nm, suggesting that Tripe-NT is a typical AIEgen with twisted intramolecular charge transfer (TICT) characteristic (FIG. 11C). The plotting of relative PL intensity (I/o) of TriPE-NT at different water fractions demonstrated its AIE activity (FIG. 11D). The aggregation behavior of TriPE-NT was characterized by field emission scanning electron microscope (FE-SEM) (FIGS. 12A-B). The nanoaggregates of the TriPE-NT showed good homogeneity at a concentration of 10 μM (FIG. 11*e*, FIG. 12). Under SEM, the nanoaggregates showed excellent dispersity and a size of approximately 15-40 nm (FIG. 11E), which further corroborated the aggregates formation of TriPE-NT (FIG. 13). To gain more insights into the photophysical properties of TriPE-NT, molecular simulation at the DFT B3LYP/6-31G* level with the Gaussian 09 package was carried out. The electron density distribution of the highest occupied molecular orbitals (HOMOs) were mainly delocalized over the TriPE part of the molecules, whereas that of the lowest unoccupied molecular orbitals (LUMOs) were localized on the naphthalimide groups, which undoubtedly demonstrated the twisted intramolecular charge transfer (TICT) effect (FIG. 14).

Example 3

TriPE-NT Sensitized ROS Generation

Figures 15A, 15B, 15C, 15D, 15E, 15F:
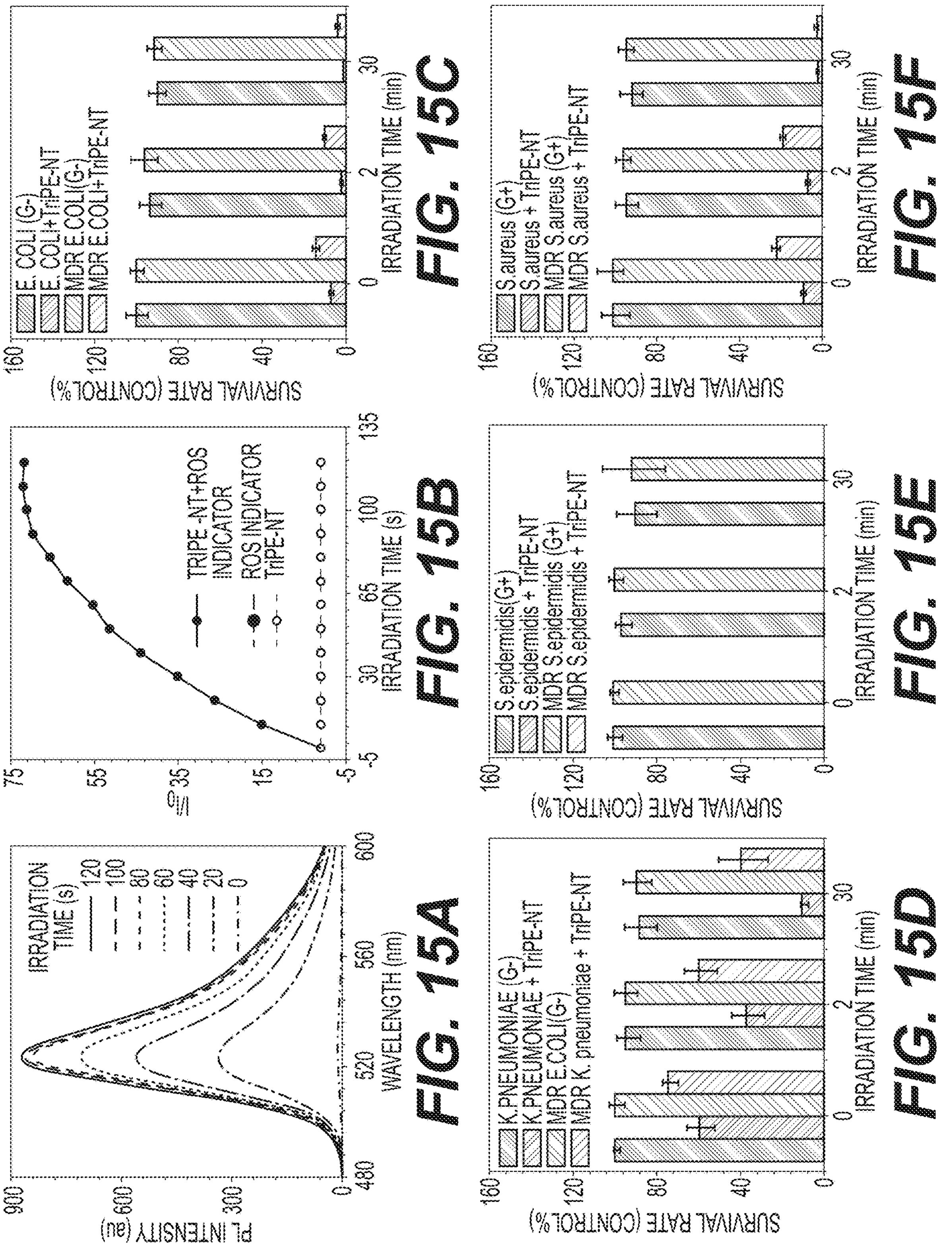
FIG. 15A is a graph plotting photoluminescence (PL) spectra of dichlorodihydrofluorescein (DCFH) indicating the generation of ROS by TriPE-NT (10 μM) after white light irradiation (4 mW $cm^{-2}$) for different time periods with an excitation wavelength of 385 nm.
FIG. 15B is a graph plotting relative PL intensity ($I/I_0$) at 385 nm versus the irradiation time, including the bacteria survival rates of *E. coli* and MDR *E. coli.*
FIGS. 15C-F are graphs depicting bacteria survival rates for bacteria that were incubated with TriPE-NT (10 μM) for 10 min, the bacteria suspensions (50 μL) were plated on agar plates and treated by white-light illumination (4 mW $cm^{-2}$) for 0, 2 and 30 min respectively.

Traditional PSs such as porphyrin usually show reduced ROS generation in the aggregated state due to the π-π stacking-increased non-radiative decay, which can greatly quench the lowest singlet state ($S_1$). In this context, AIEgens as PSs can offer high ROS production efficiency in the aggregated state, since the twisted structure of AIEgens can effectively avoid the π-π stacking-caused $S_1$ quenching. On the other hand, AIEgens with TICT characteristic have been demonstrated to facilitate effective $^1O_2$ producing. ROS generation by using dichlorofluorescein (DCFH), a commercially available ROS indicator, was subsequently tested. The fluorescence of DCFH will be lit-up if it is in the presence of ROS species. As shown in FIG. 15A, under white light irradiation, DCFH showed negligible emission in the visible region. However, in the presence of both DCFH and TriPE-NT with white light irradiation, DCFH exhibited gradually increased fluorescence at around 530 nm (FIG. 15B), demonstrating that TriPE-NT as a photosensitizer can generate ROS under white light irradiation.

Example 4

Light-Enhanced Bacteria Killing

Figure 16B:
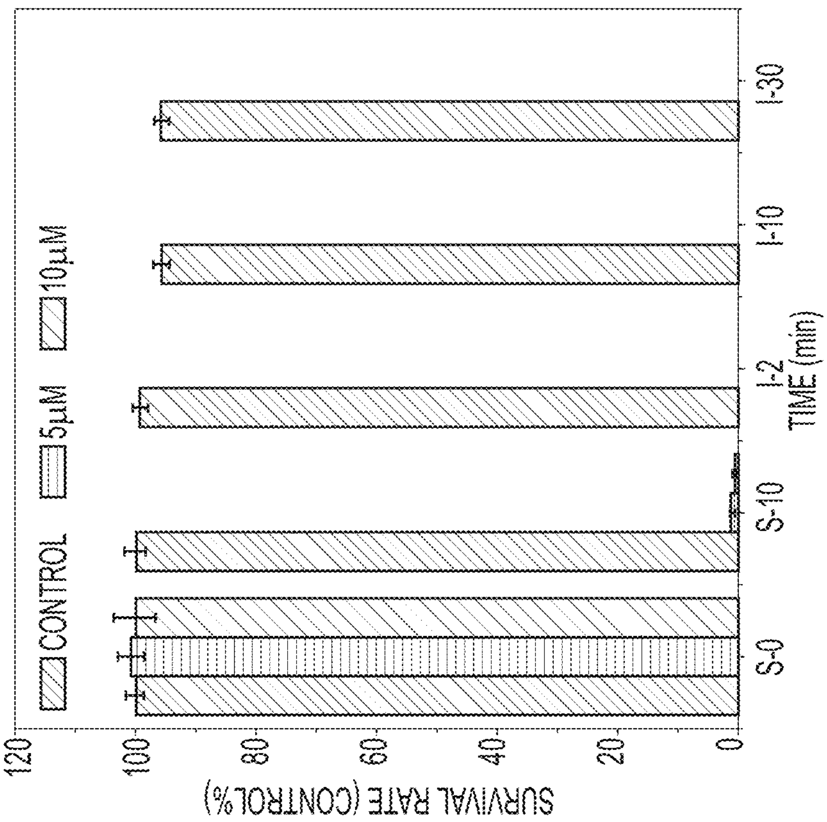
FIGS. 16A-B are graphs depicting bacteria survival rates for bacteria that were incubated with TriPE-NT (0, 5, 10 μM) for 0 (S-0) and 10 (S-10) min, the bacteria suspensions (50 μL) were plated on agar plates and treated by white-light illumination (4 mW $cm^{-2}$) for 2 (I-2), 10 (I-10) and 30 (I-30) min respectively.
Figure 16A:
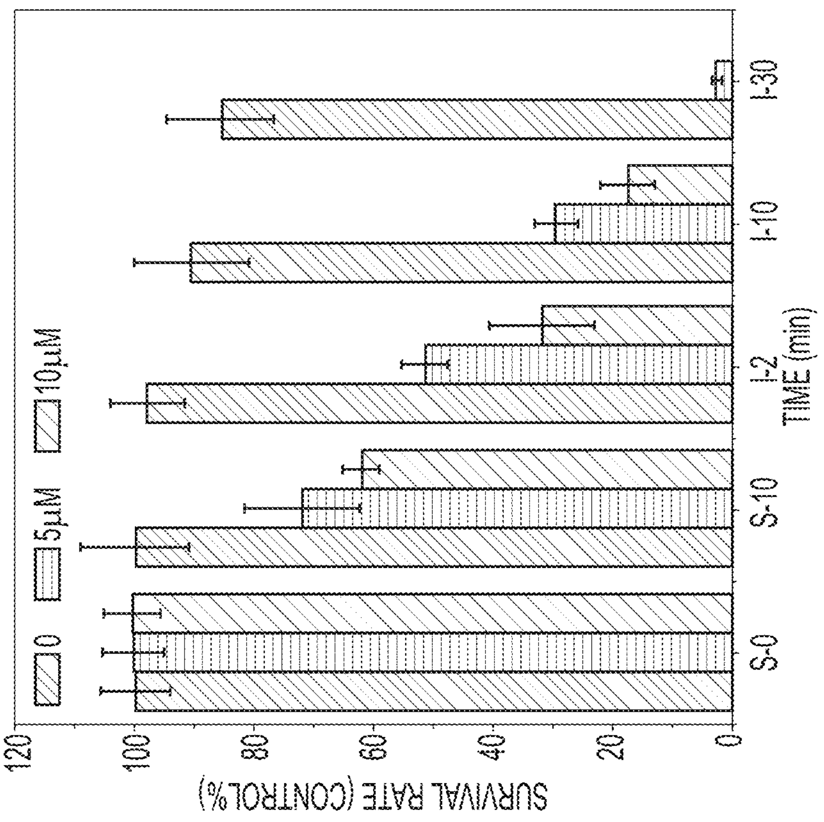

The bacteria killing effect of TriPE-NT was evaluated on both wild and clinically isolated MDR bacteria by a traditional plate counting method. First, *E. coli* and *S. epidermidis*, as the representative of Gram-negative (G−) and Gram-positive (G+) bacteria, were used to determine the effective bactericidal concentration and illumination time. The bacteria were incubated with TriPE-NT (0, 5, 10 μM) for 0 and 10 min, the bacteria suspensions (50 μL) were plated on agar plates and treated by white-light illumination (4 mW $cm^{-2}$) for 2, 10 and 30 min respectively (FIGS. 16A-B). TriPE-NT at a concentration of 10 μM (8.4 g $mL^{-1}$) killed all *E. coli* after white light irradiation of 30 min, while all *S. epidermidis* were killed by a lower TriPE-NT concentration (5 μM, 4.2 g $mL^{-1}$) after light irradiation of 2 mm. Thus, 10 μM TriPE-NT and light irradiation for 2 min or 30 min were set as experimental conditions in the following experiments.

Figure 17C:
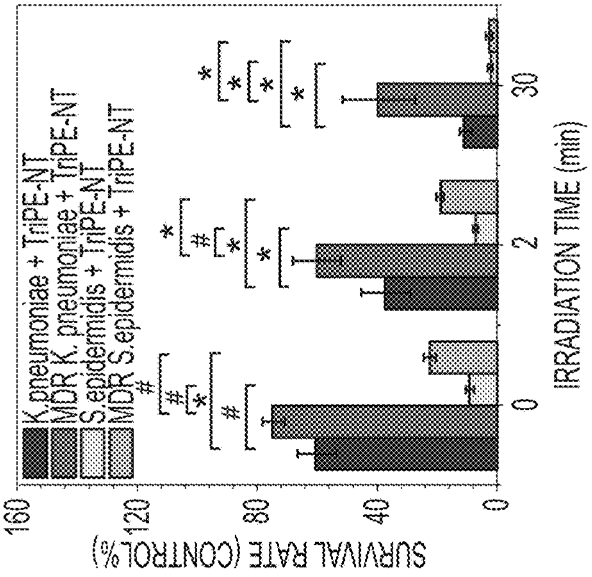
FIGS. 17A-C are graphs depicting bacteria survival rate comparison for bacteria that were incubated with TriPE-NT (10 M) for 10 min, the bacteria suspensions (50 μL) were plated on agar plates and treated by white-light illumination (4 mW $cm^{-2}$) for 0, 2 and 30 min respectively (0.001<*P<0.05, #P<0.001).
Figure 17B:
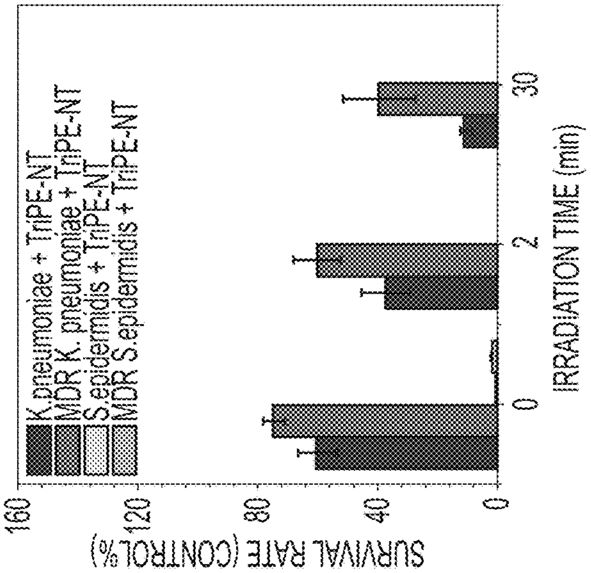
Figure 17A:
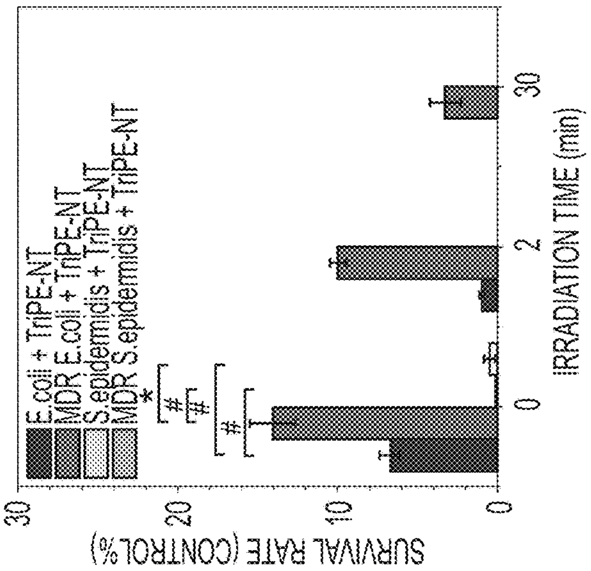

As for Gram-negative bacteria *E. coli*, MDR *E. coli, K. pneumoniae*, MDR *K. pneumoniae*, and Gram-positive bacteria *S. epidermidis*, MDR *S. epidermidis, S. aureus* and MDR *S. aureus*, colony counting showed that TriPE-NT had potent light-enhanced antibacterial activity (FIGS. 15C-F). In darkness, 10 μM (8.4 g $mL^{-1}$) TriPE-NT killed nearly all MDR *S. epidermidis* (FIG. 15E, 0 min), while the survival rates of *E. coli*, MDR *E. coli, K. pneumoniae*, MDR *K. pneumoniae, S. aureus* and MDR *S. aureus* were approximately 6.8±0.6%, 14.1±1.4%, 59.9±6.5%, 74.4±3.7%, 8.9±1.1% and 22.4±1.9%, respectively (FIGS. 15C, D, F). Therefore, TriPE-NT itself can work as a superior antibiotic. Under irradiation with white light (4 mW $cm^{-2}$, 30 min), all *E. coli* and more than 96% MDR *E. coli,* 90% *K. pneumoniae,* 61% MDR *K. pneumoniae,* 98% *S. aureus* and 97% MDR *S. aureus* were killed (FIGS. 15C, D, F), indicating light irradiation can further promote the antibacterial activity of TriPE-NT even for MDR bacteria. TriPE-NT agents plus light irradiation were more effective to inhibit *S. epidermidis* or MDR *S. epidermidis* than *E. coli* MDR *E. coli, K. pneumoniae* or MDR *K. pneumoniae* (FIGS. 17A-B). Also, *S. aureus* and MDR *S. aureus* were more susceptible to TriPE-NT plus light irradiation than *K. pneumoniae* or MDR *K. pneumoniae* (FIG. 17C). By comparison, polymyxin, the last line treatment for MDR Gram-negative bacterial infections, showed antibacterial activity to MDR *E. coli* and MDR *K. pneumoniae*, at a minimum inhibition concentration (MIC) surpassing 32 or 64 μg $mL^{-1}$ respectively, see Table 1 below:

TABLE 1

Antibacterial activities indicated by MIC (μg $mL^{-1}$). *E. coli*, *K. pneumoniae*, *S. epidermidis* and *S. aureus* are laboratory-sensitive strains. MDR *E. coli*, MDR *K. pneumoniae*, MDR *S. aureus* and MDR *S. epidermidis* are clinical MDR isolates. MIC is the minimal concentration at which no visible bacterial growth is observed in all three parallels. Penicilin (Pen), Gentamicin (Gen), Polymyxin (Pol).

| | Pen | Gen | Pol |
|---|---|---|---|
| Gram-Negative Bacteria | | | |
| *E.coli* | <2 | <2 | 16 |
| MDR *E.coli* | >128 | >128 | 32 |
| *K. pneumoniae* | 32 | <2 | <2 |
| MDR *K. pneumoniae* | >128 | >128 | 64 |
| Gram-Positive Bacteria | | | |
| *S. epidermidis* | <2 | <2 | 64 |
| MDR *S. epidermidis* | >32 | <2 | >128 |
| *S. aureus* | <2 | <2 | >128 |
| MDR *S. aureus* | 64 | >128 | >128 |

In contrast, as shown in 15C-F, TriPE-NT effectively inhibited not only Gram-negative bacteria but also Gram-positive bacteria at a relatively low concentration, demonstrating its superior antibacterial activities over conventional antibiotics.

Figure 18B:
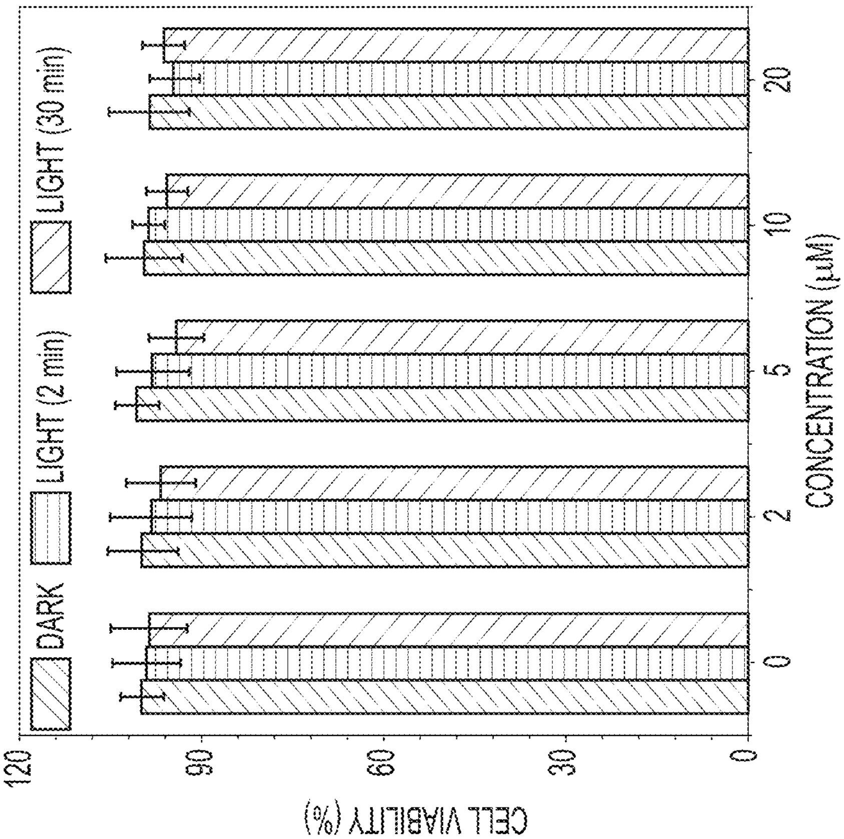
FIGS. 18A-B are graphs depicting cell viability of human amniotic fluid stem cells (HAFs) and human umbilical vein endothelial cells (HUVECs) after incubation with TriPE-NT at different concentrations of 0, 2, 5, 10 and 20 μM under dark conditions and upon white-light illumination (4 mW $cm^{-2}$) for 2 and 30 min.
Figure 18A:
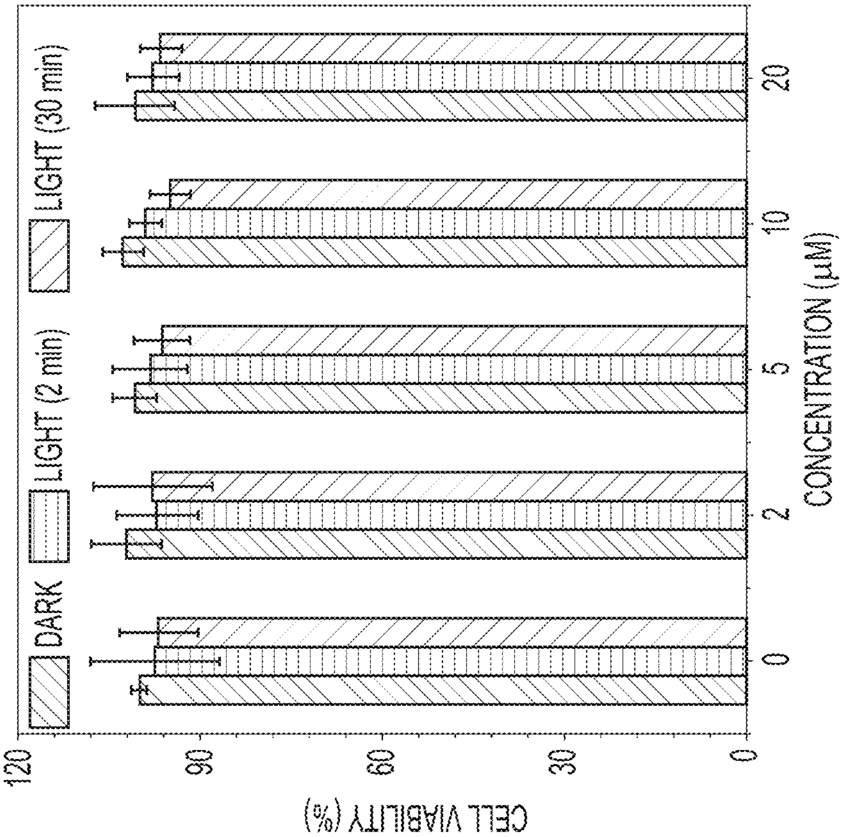

Cytotoxicity of the TriPE-NT was tested because a good antibacterial drug should have the ability to kill only bacteria and have no toxicity to human or animal cells. The biocompatibility of TriPE-NT was evaluated by CCK-8 kit. The cell viabilities of human skin fibroblast cells (HAFs) and human umbilical vein endothelial cells (HUVECs) were not significantly changed with the increasing concentration of TriPE-NT (2, 5, 10 and 20 RM) in the absence of white light irradiation (4 mW $cm^2$), and no obvious cytotoxicity was observed with the increase of irradiation time (FIGS. 18A-B), demonstrating the high safety of TriPE-NT for mammalian cells.

Example 5

Bacteria Staining and Imaging

Figure 19B:
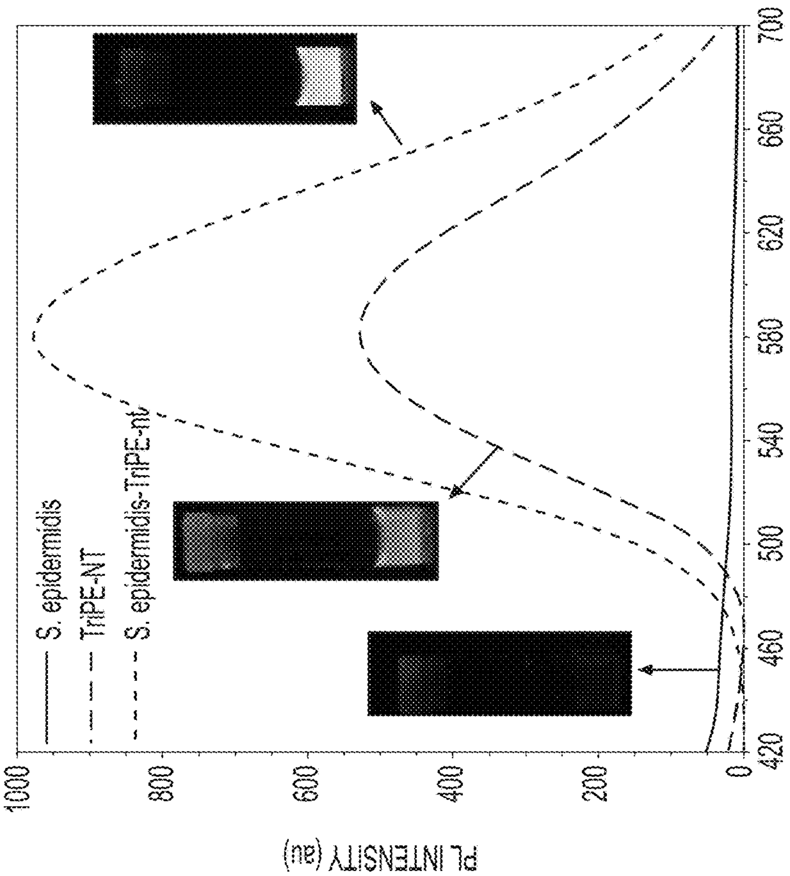
FIG. 19B is a graph plotting the PL spectra of *S. epidermidis* and TriPE-NT (10 μM) with and without *S. epidermidis* ($10^9$ CFU $mL^{-1}$) which includes images of *S. epidermidis*, TriPE-NT, and TriPE-NT and *S. epidermidis* mixture taken under 365 nm UV irradiation
Figure 19A:
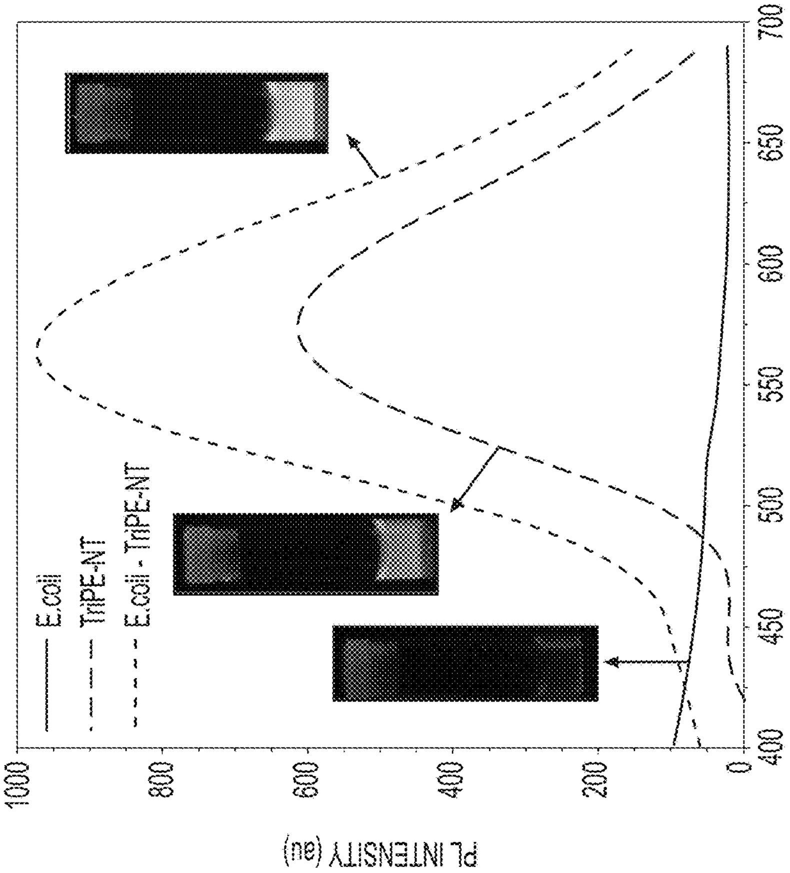
FIG. 19A is a graph plotting the PL spectra of *E. coli* and TriPE-NT (10 μM) with and without *E. coli* ($10^9$ CFU $mL^{-1}$) which includes images of *E. coli*, TriPE-NT, and TriPE-NT and *E. coli* mixture taken under 365 nm UV irradiation

To understand how TriPE-NT works, the bacteria was stained with TriPE-NT. The pure solution of *E. coli* (G−) or *S. epidermidis* (G+) showed weak blue color under 365 nm UV irradiation, while the pure TriPE-NT (10 μM) was orange under the same irradiation. After incubation with 10 μM TriPE-NT for 10 min, the solution containing *E. coli* or *S. epidermidis* emitted strong yellow fluorescence under 365 nm UV irradiation (FIGS. 19A-B).

Figure 20:
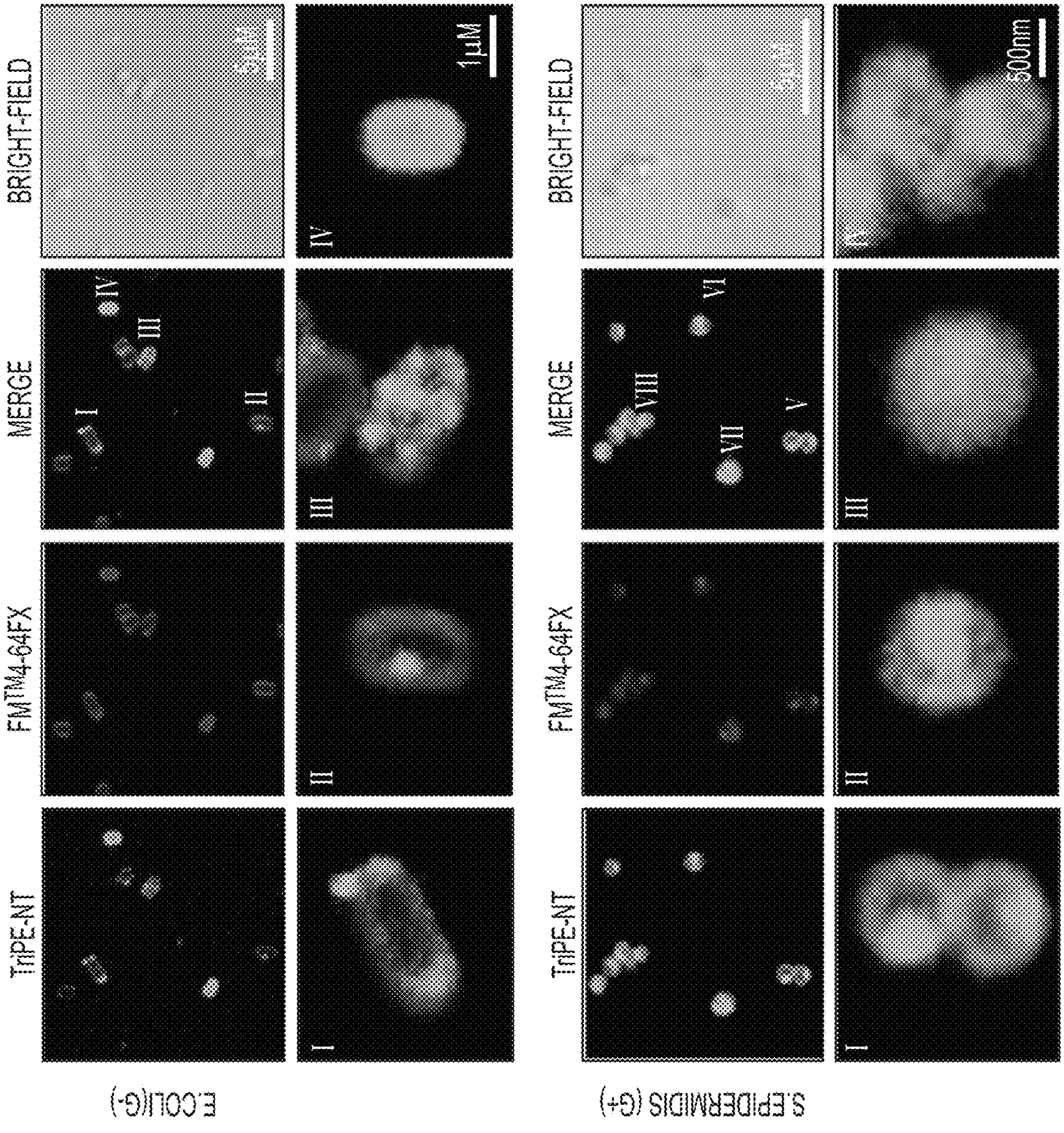
FIG. 20 shows bright-field and fluorescent images of *E. coli* (G−) and *S. epidermidis* (G+) incubated with 10 μM of TriPE-NT and FM™ 4-64FX for 10 min. TriPE-NT: Ex, 405 nm, Em, 500-560 nm; FM™ 4-64FX: Ex, 543 nm, Em, 600-700 nm.

To directly observe the interactions between TriPE-NT and the bacteria, the bacteria was co-incubated with TriPE-NT and FM™4-64FX (a lipid membrane dye) and fluorescence imaging was conducted using confocal laser scanning microscopy (CLSM). For most of the *E. coli*, TriPE-NT only stained the cell membrane (FIG. 20, I-IV). By contrast, for *S. epidermidis*, the probe lit up almost the whole bacteria, including the membrane and the cytosol (FIG. 20, V-VIII). This phenomenon implies that it may be easier for TriPE-NT to penetrate into *S. epidermidis* than into *E. coli*, as the latter contains an extra outer membrane.

Figure 21A:
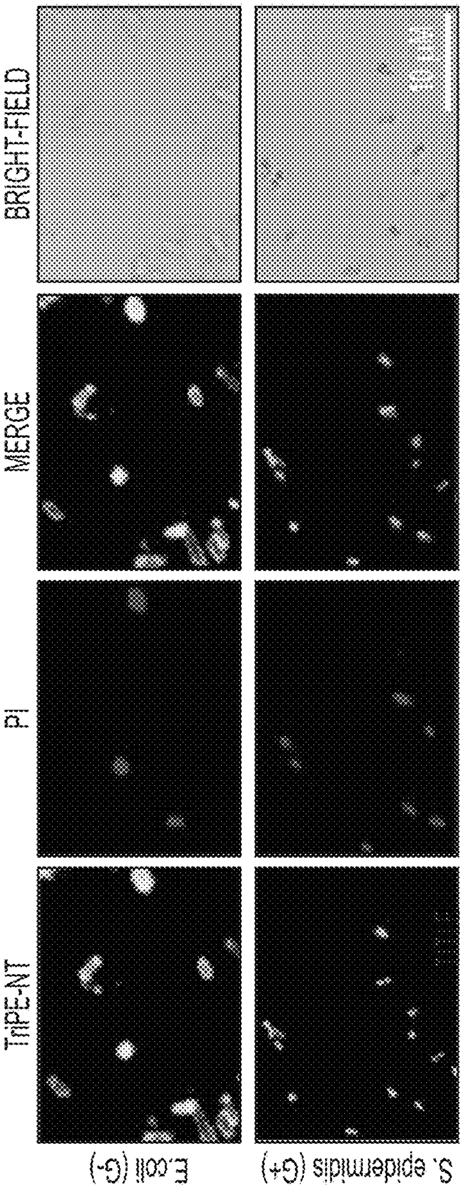
FIG. 21A shows bright-field and fluorescent images of *E. coli* and *S. epidermidis* incubated with 10 μM of TriPE-NT and propidium iodide (PI) for 10 min. TriPE-NT: Ex, 405 nm, Em, 500-560 nm; PI: Ex, 514 nm, Em, 600-700 nm.
Figure 21B:
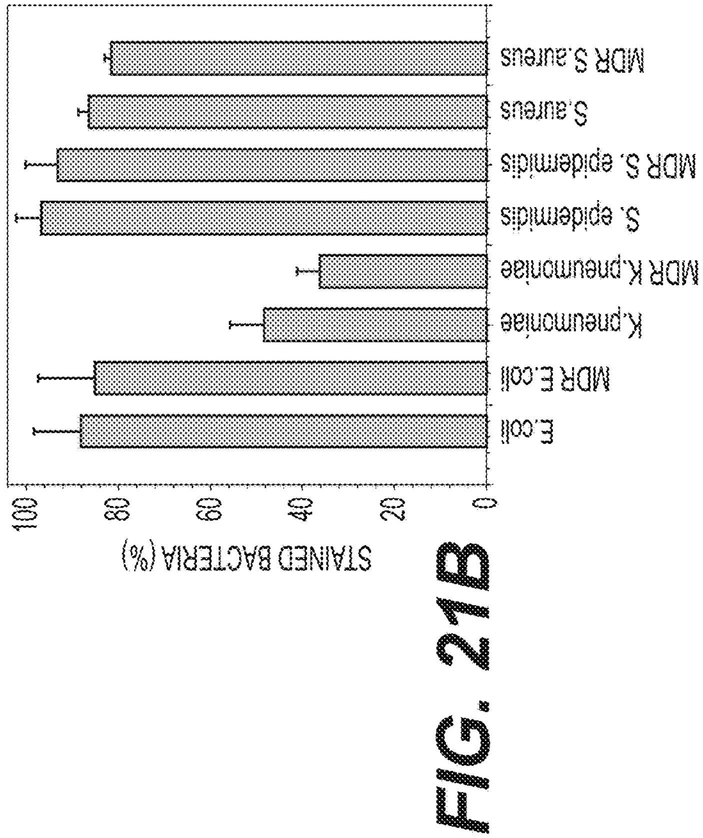
FIG. 21B is a graph plotting stained percentages for *E. coli*, MDR *E. coli, K. pneumoniae*, MDR *K. pneumoniae, S. epidermidis*, MDR *S. epidermidis, S. aureus*, and MDR *S. aureus.*
Figure 21C:
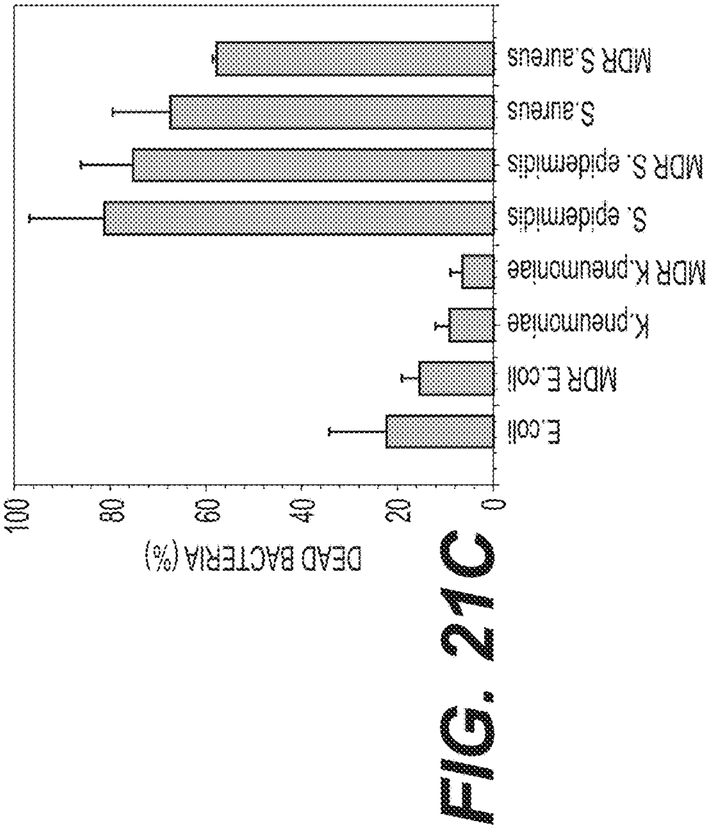
FIG. 21C is a graph plotting percentage of dead bacteria stained by propidium iodine (PI) after the bacteria were incubated with 10 μM of TriPE-NT or PI for 10 min.
Figure 22:
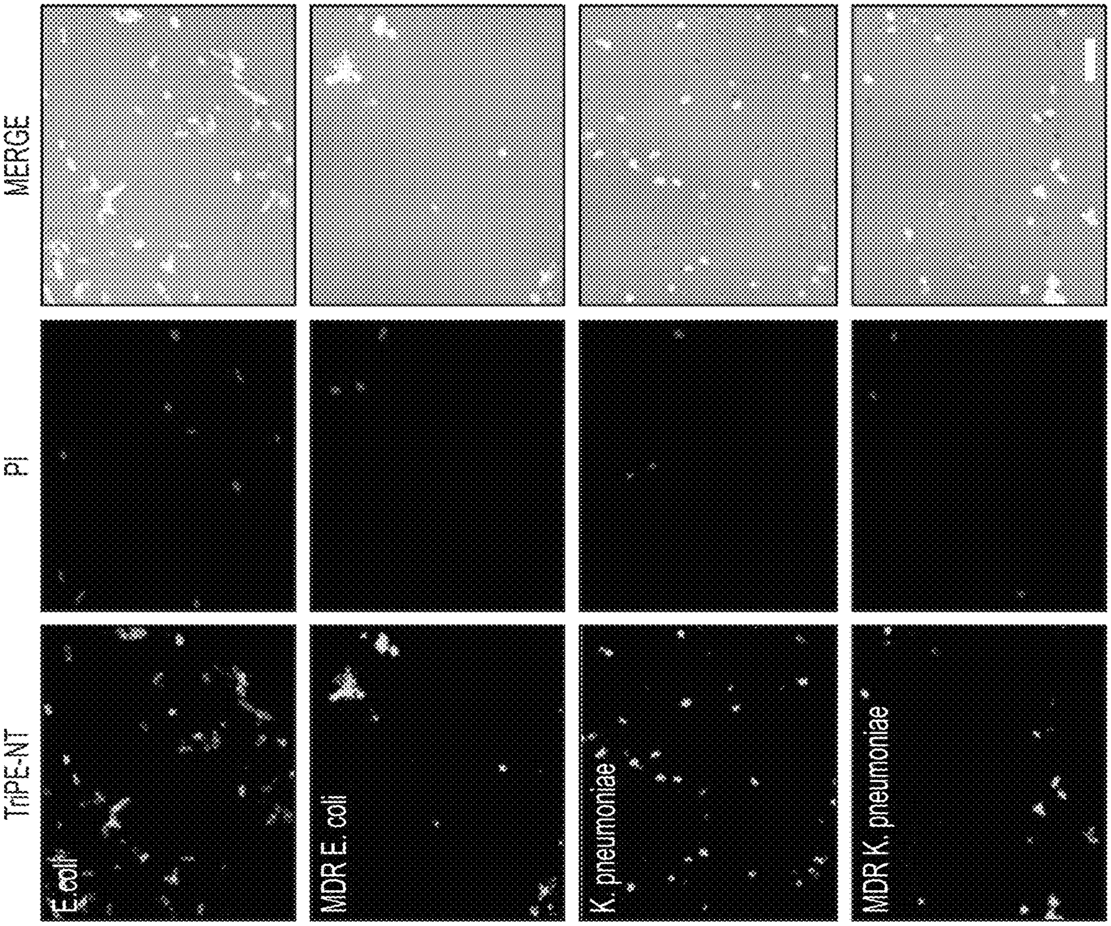
FIG. 22 shows bright-field and fluorescent images of *E. coli*, MDR *E. coli, K. pneumoniae*, MDR *K. pneumoniae* incubated with 10 μM of TriPE-NT and propidium iodide (PI) for 10 min. TriPE-NT: Ex=405 nm, Em=500-560 nm; PI: Ex=514, Em=600-700. The scale bar is equal to 5 μm.
Figure 23:
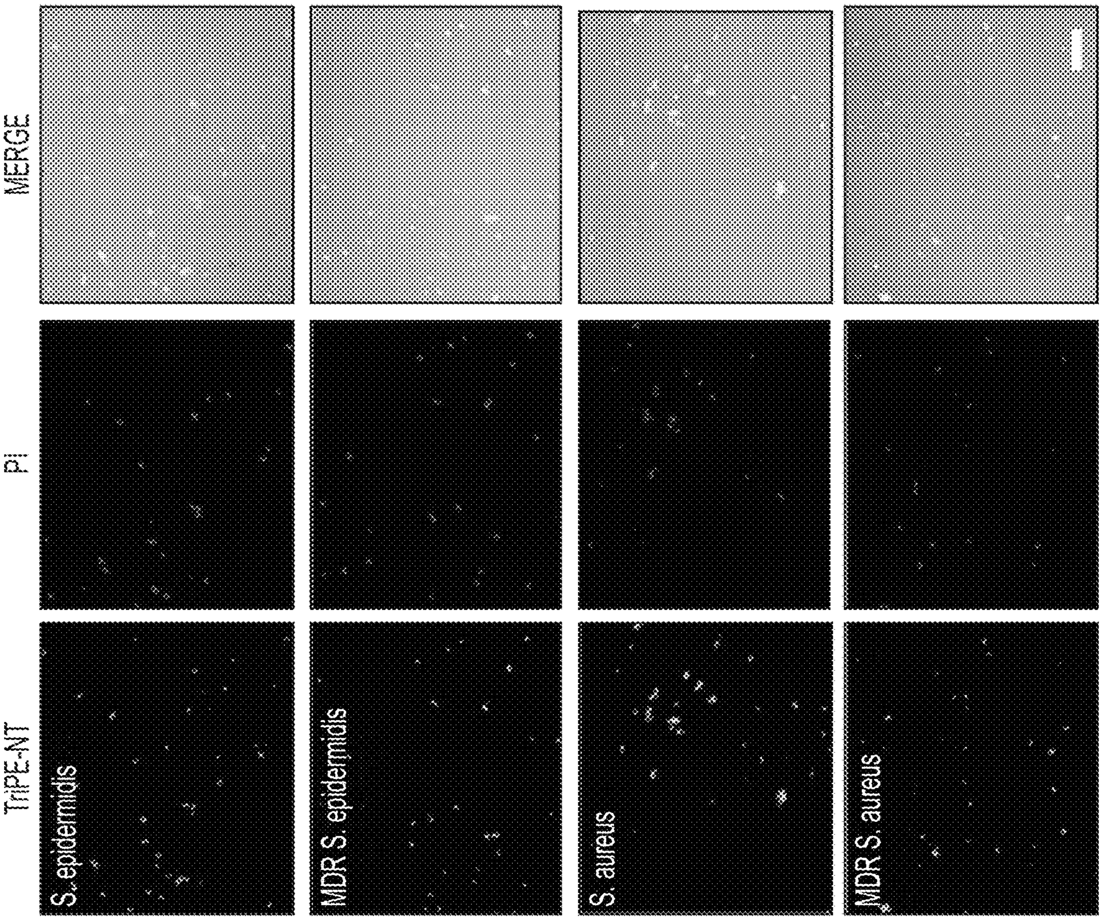
FIG. 23 shows Bright-field and fluorescent images of *S. epidermidis*, MDR *S. epidermidis, S. aureus* and MDR *S. aureus* incubated with 10 μM of TriPE-NT and propidium iodide (PI) for 10 min with the scale bar equal to 5 μm. TriPE-NT: Ex=405 nm, Em=500-560 nm; PI: Ex=514, Em=600-700.

To indicate the status of the bacteria after TriPE-NT treatment, the bacteria was incubated with commercial dead bacteria-staining fluorescent reagent propidium iodide (PI) and TriPE-NT at the same time. Thanks to the AIE characteristics and water solubility of TriPE-NT, there was almost no background fluorescence in the imaging field. *E. coli* and *S. epidermidis*, which emitted bright orange (TriPE-NT) or red (PI) fluorescence, are clearly visualized under confocal laser scanning microscope (CLSM) (FIG. 21A-C, 22-23). It was found that TriPE-NT can stain almost all the Gram-positive bacteria (e.g., 96.2±5.6% *S. epidermidis,* 92.9±6.6% MDR *S. epidermidis,* 86.1±1.9% *S. aureus* and 80.9±1.7% MDR *S. aureus*) (FIG. 21A-C, FIG. 23), no matter whether they were alive or dead (red). In comparison, relatively low percentage of Gram-negative bacteria were stained by TriPE-NT (e.g., 88.1±9.8% *E. coli,* 84.3±12.7% MDR *E. coli,* 47.9±7.7% *K. pneumoniae* and 35.8±4.9% MDR *K. pneumoniae*) (FIG. 21B, FIG. 22). Notably, almost all the *S. epidermidis* (80.9±15.8% *S. epidermidis*) were co-stained by TriPE-NT and PI (FIGS. 21A, C), this is similar to other Gram-positive bacteria (74.8±11.4%, MDR *S. epidermidis,* 67.3±12.2%, *S. aureus* and 57.4±1.3%, MDR *S. aureus*) (FIG. 22, FIGS. 21A, C). By contrast, relatively low percentages of *E. coli* (22.1±12.2% *E. coli*) were co-stained by both TriPE-NT and PI (FIGS. 21A, C), which is also similar to other Gram-negative bacteria (15.3±3.7%, MDR *E. coli,* 8.8±3.2%, *K. pneumoniae* and 6.4±2.6% MDR *K. pneumoniae*) (FIGS. 21A & C, 22). The reason for this difference possibly is ascribed to the extra membrane of Gram-negative bacteria which is absent in Gram-positive bacteria. These observations also illustrated that both Gram-negative bacteria and Gram-positive bacteria are vulnerable to TriPE-NT treatment, the possible reason is that these bacteria with negatively charged membranes, could anchor, uptake, and aggregate the positively charged probe, which restricts the intramolecular motion of the probe and causes their fluorescence emission.

Example 6

FE-SEM and FEHR-TEM

Figure 24A:
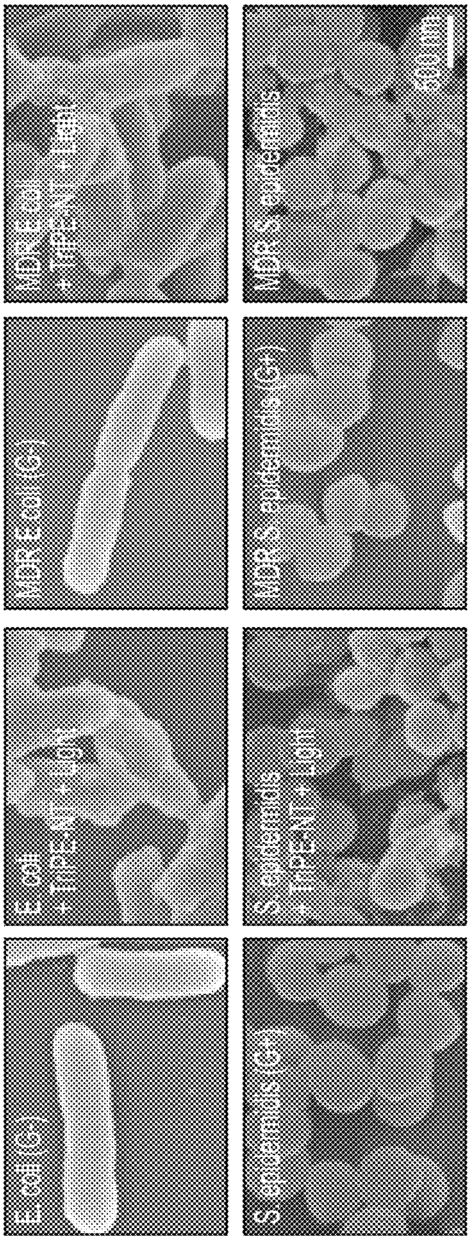
FIGS. 24A-E show images of TriPE-NT-induced morphological changes of *E. coli*, MDR *E. coli, S. epidermidis* and MDR *S. epidermidis* with white light irradiation by FE-SEM and FEHR-TEM, bacteria without treatment were set as controls.
Figure 24B:
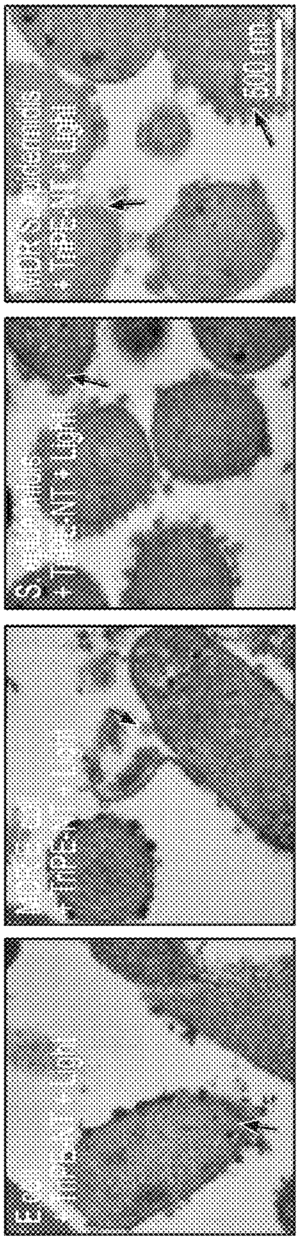
Figure 25:
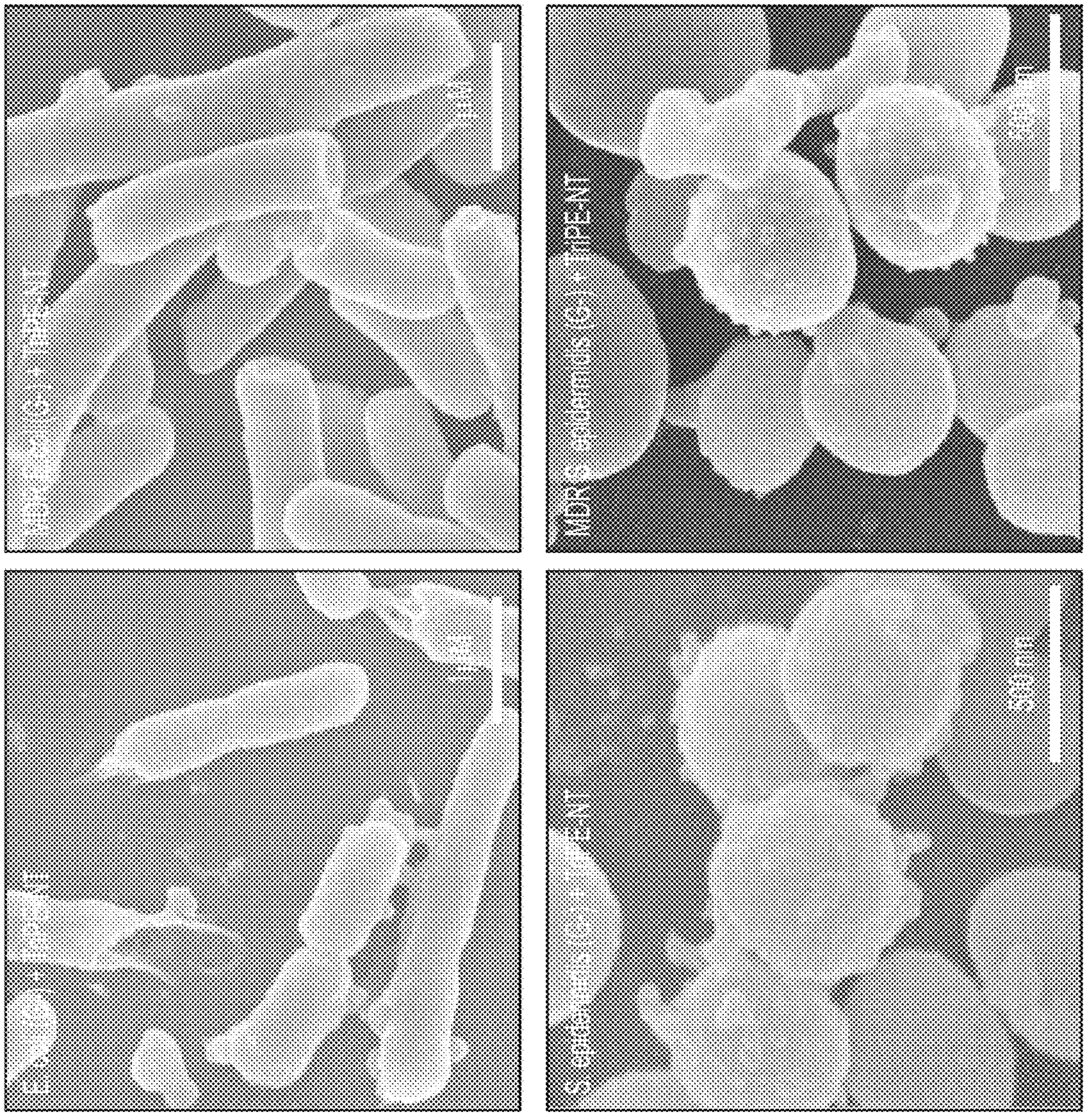
FIG. 25 shows images of the morphology of *E. coli*, MDR *E. coli, S. epidermidis*, and MDR *S. epidermidis* treated by TriPE-NT without light irradiation.

To gain more insights into the TriPE-NT-bacteria interactions, FE-SEM and field-emission high resolution transmission electron microscope (FEHR-TEM) were used to visualize the morphological changes of the bacteria under TriPE-NT treatment, selecting *E. coli* (G−), MDR *E. coli* (G−), and *S. epidermidis* (G+), MDR *S. epidermidis* (G+) as representatives. Without TriPE-NT treatment, the four kinds of bacteria showed regular shape with clear borders and cell walls (FIG. 24A). *E. coli* or MDR *E. coli* treated by TriPE-NT in the absence of white light showed an obvious rough surface and damaged cell wall (FIG. 25), and light irradiation further exacerbated the damage where cell wall fragmentations can be observed (FIG. 24A). For *S. epidermidis* and MDR *S. epidermidis*, TriPE-NT treatment without or with light irradiation (4 mW $cm^{-2}$, 30 min) led to a wrinkled bacterial cell wall (FIGS. 24A, 25). Parts of TriPE-NT-treated bacteria showed broken cell walls (arrows) and many granular substances on the surface of the bacteria (FIG. 24B).

Example 7

Elemental Scan Analysis

Figure 24C:
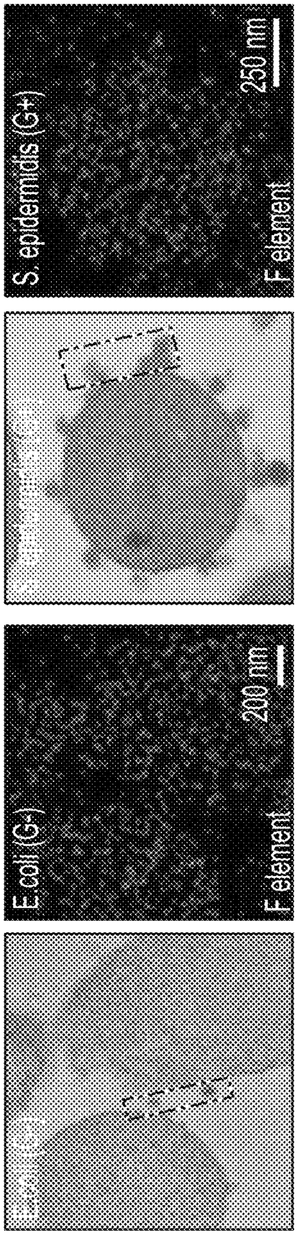
Figure 24D:
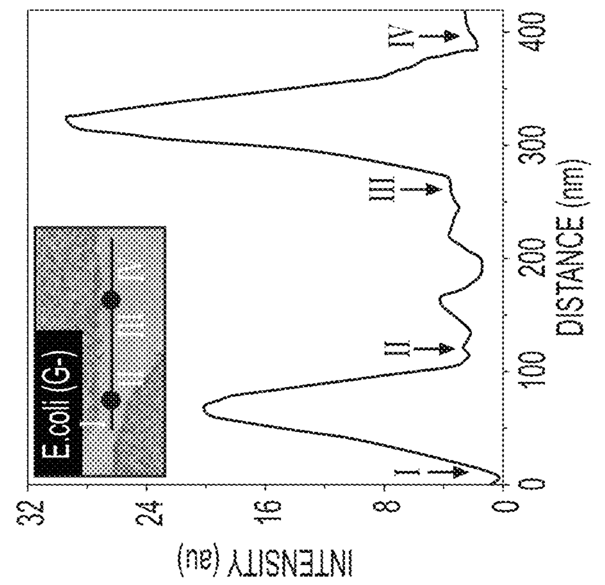
Figure 24E:
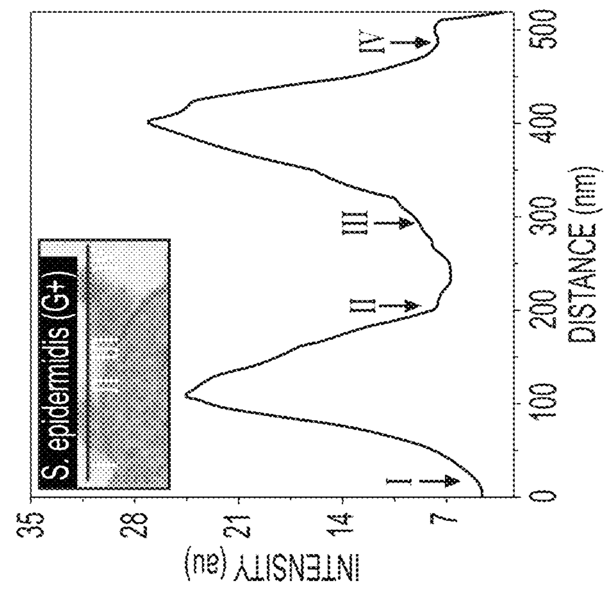

Elemental scan analysis was used on bacterial super-thin slices (60-70 nm in thickness) to verify if TriPE-NT can enter bacterial cells. Bacteria are usually composed of elements including carbon (C), nitrogen (N), and oxygen (O), while the TriPE-NT molecule is composed of C, N, O and fluorine (F) elements. In this study, the distribution of F elements in the TriPE-NT-treated *E. coli* and *S. epidermidis* was analyzed. The imaging (FIG. 24C) and signal analysis (FIGS. 24D, E) demonstrated that both *E. coli* and *S. epidermidis* showed the signals of F element which was contributed by TriPE-NT. The results indicate that TriPE-NT can attach on the cell wall or enter into the bacteria.

Example 8

Evaluation on Rat Wound Models

Figure 26A:
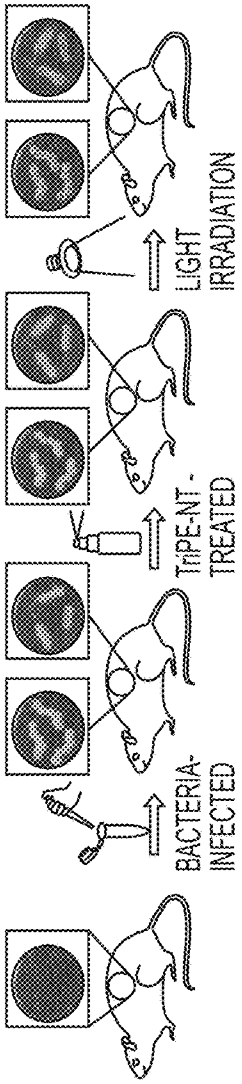
FIGS. 26A-D show In vivo evaluation of TriPE-NT in treatment of bacteria-infected wounds on rats.
Figure 26B:
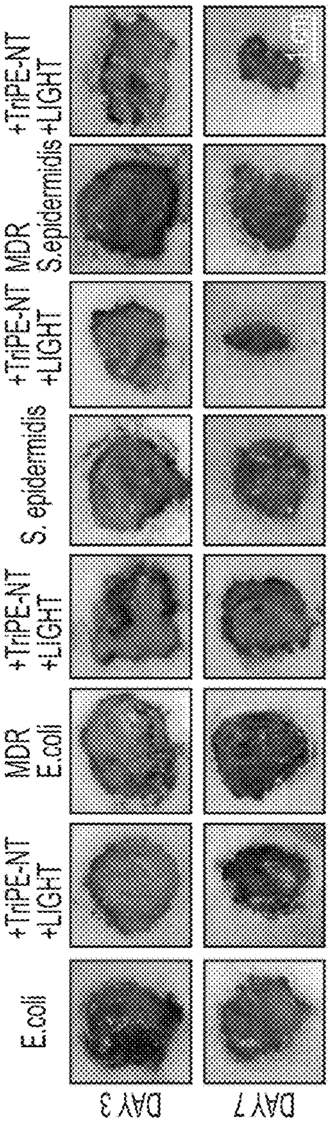
Figure 26C:
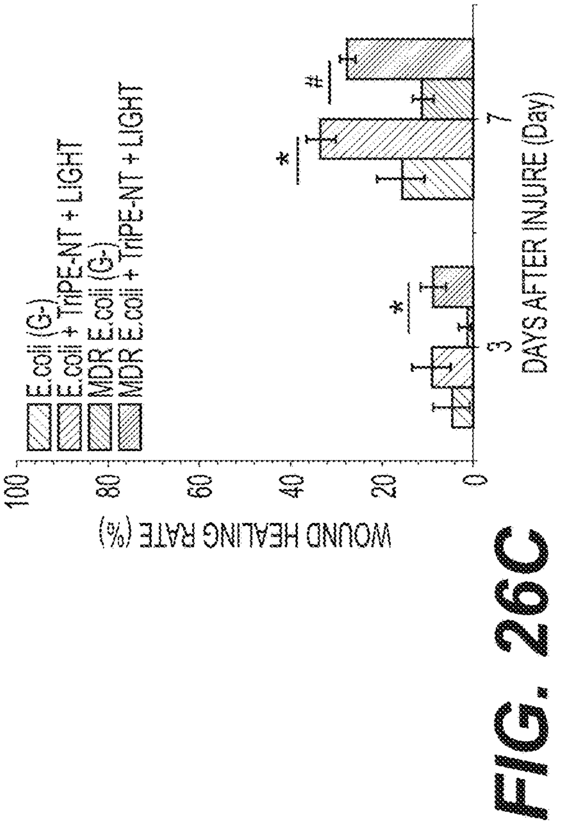
Figure 26D:
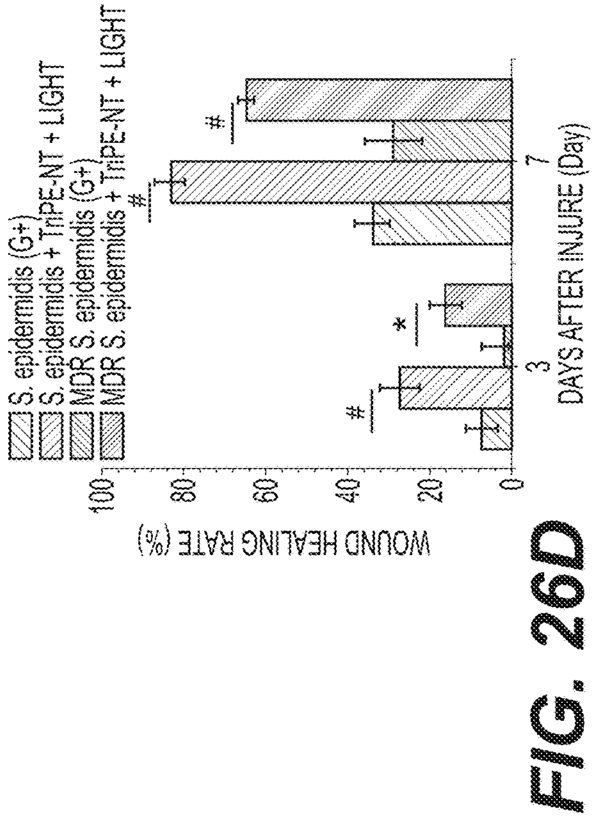
Figure 27:
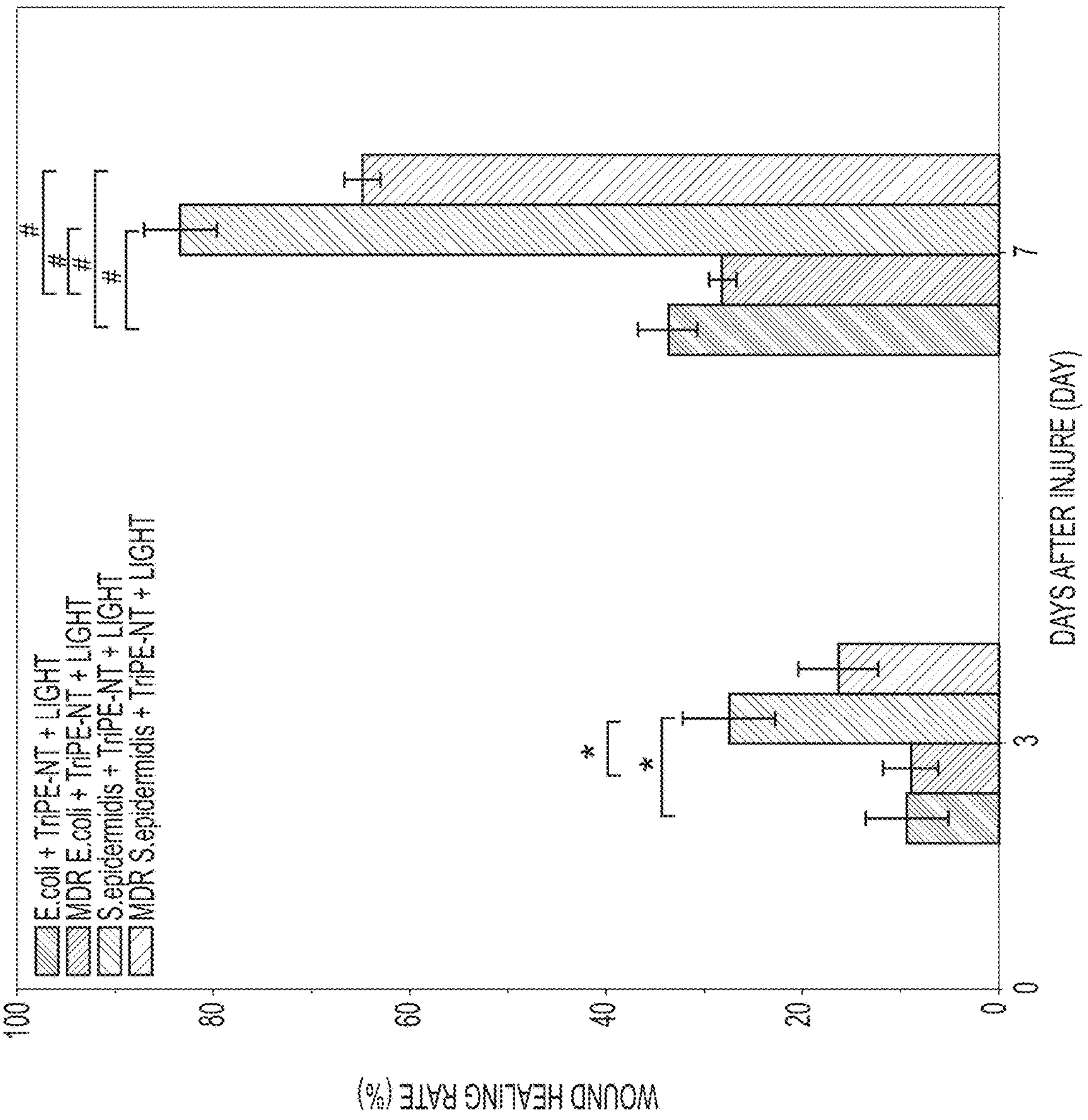
FIG. 27 is a graph plotting the proportion of the *E. coli*-, MDR *E. coli*-, *S. epidermidis*- and MDR *S. epidermidis*-infected wound area on day 3 and day 7 after the injury (each experiment was repeated at least 5 times).

To further evaluate the anti-bacterial activity of TriPE-NT in vivo, the performance of TriPE-NT on bacteria-infected wounds of rats was tested. *E. coli*-, MDR *E. coli*-, *S. epidermidis* or MDR *S. epidermidis*-infected, full-thickness skin wounds were established on the dorsal skin of the Wistar rats (FIG. 26A). The macroscopic appearance of the healing processes of the wounds was captured at different time points (FIG. 26B). On day 3 post-injury, all the wounds showed no apparent difference (FIG. 26C). On day 7, the sizes of the MDR *E. coli*-infected wounds treated by TriPE-NT plus light irradiation (4 mW $cm^{-2}$, 30 min) were significantly smaller than those of the control groups respectively, while *E. coli*-infected wounds treated by TriPE-NT agents plus light had more apparent reduction of wound size on day 7 post-injury (FIG. 26C). MDR *S. epidermidis*-infected wounds treated by TriPE-NT agents plus light irradiation (4 mW $cm^{-2}$, 30 min) showed significantly smaller sizes than the control groups on day 7 post-injury, while the *S. epidermidis*-infected wounds treated by TriPE-NT agents plus light irradiation showed more apparent reduction of wound size on day 7 post-injury (FIG. 26D). By comparison, under the same TriPE-NT plus light irradiation, *S. epidermidis* or MDR *S. epidermidis*-infected wounds showed a faster healing rate than *E. coli* or MDR *E. coli*-infected wounds (FIG. 27). The result agrees with the in vitro testing that TriPE-NT agents plus light irradiation were more effective to inhibit *S. epidermidis* or MDR *S. epidermidis* than *E. coli* or MDR *E. coli* (FIG. 27).

Figure 28:
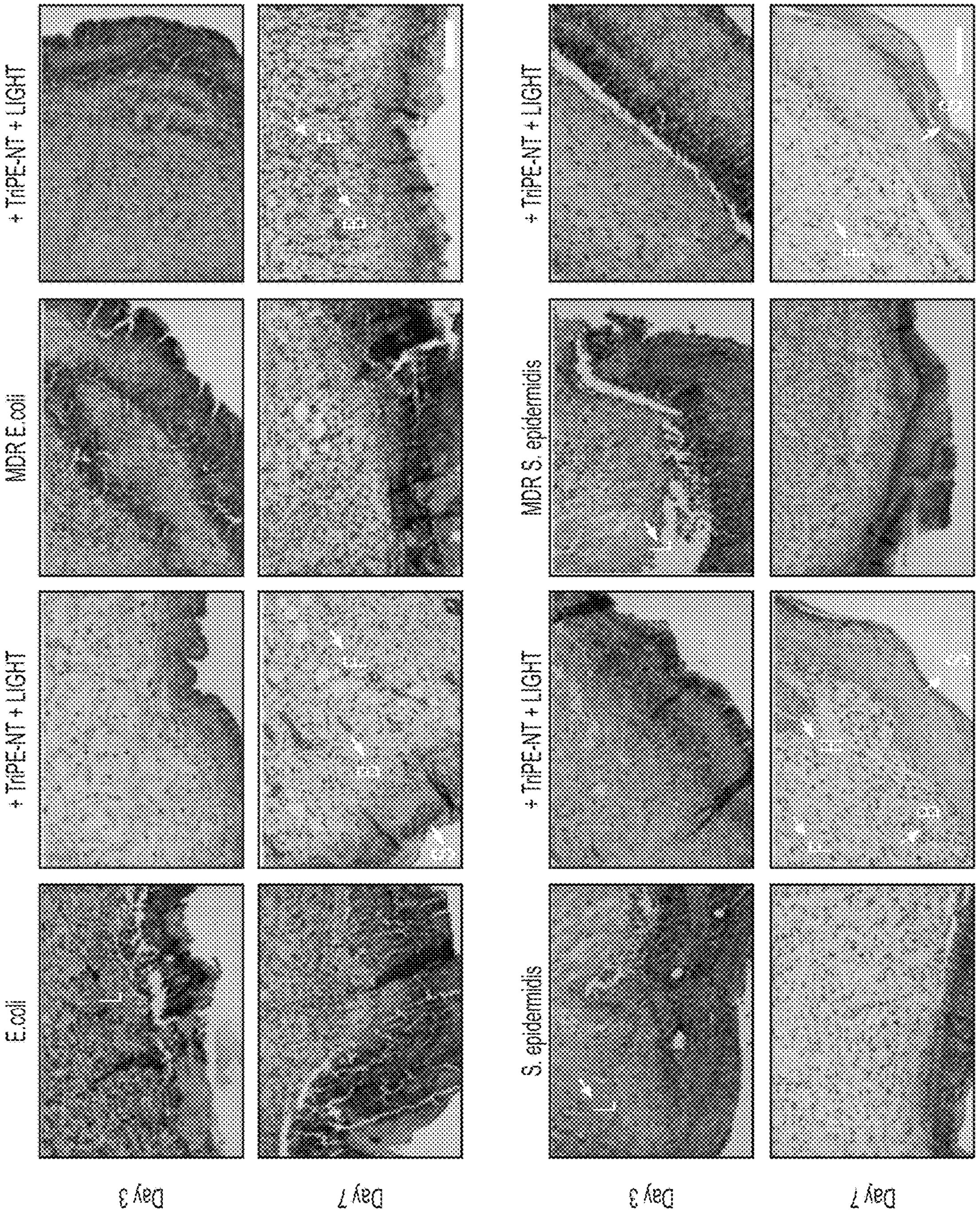
FIG. 28 shows images of hematoxylin and eosin (HE) staining of the sectioned tissues of *E. coli*, MDR *E. coli, S. epidermidis* or MDR *S. epidermidis* infected wounds treated with or without TriPE-NT plus white-light irradiation on day 3 and 7 after injury. The letters in the images indicate specific cell types and structures in the histological sections. L: lymphocytes; B: blood vessels; F: fibroblasts; S, squamous epithelial cell; H, hair follicle. All scale bars equal to 100 m.

Hematoxylin and eosin (HE) staining was carried out for evaluating the wound healing of the sectioned tissues of the *E. coli*-, MDR *E. coli*-, *S. epidermidis*- and MDR *S. epidermidis*-infected wounds on the Wistar rats on day 3 and day 7 post-injury (FIG. 28). On day 3 post-injury, the *E. coli*-, MDR *E. coli*-, *S. epidermidis*- and MDR *S. epidermidis*-infected wounds without TriPE-NT plus light irradiation treatment showed more invaded lymphocytes than the samples treated by TriPE-NT plus light irradiation, implying that TriPE-NT plus light irradiation successfully reduced the inflammatory reactions. On day 7 post-injury, *S. epidermidis*- or MDR *S. epidermidis*-infected wounds treated by TriPE-NT plus light irradiation displayed the appearance of fibroblasts and newly formed squamous epithelial layers, which can hardly be seen in the control groups. Fibroblasts can secret collagens which accelerate wound reconstruction, that means the TriPE-NT plus light irradiation can promote the wound healing. On day 7 post-injury, the bacteria-infected wounds treated by TriPE-NT plus light irradiation showed appearance of hair follicles in *S. epidermidis*-infected wounds. The in vivo experiments demonstrated that the TriPE-NT plus light irradiation had successfully suppressed the bacterial infections and promoted the wound healing.

The present subject matter being thus described, it will be apparent that the same may be modified or varied in many ways. Such modifications and variations are not to be regarded as a departure from the spirit and scope of the present subject matter, and all such modifications and variations are intended to be included within the scope of the following claims.

We claim:

1. An antibiotic compound capable of staining and killing Gram-positive and Gram-negative bacteria, comprising a compound that exhibit aggregation induced emission properties, wherein the compound comprises:

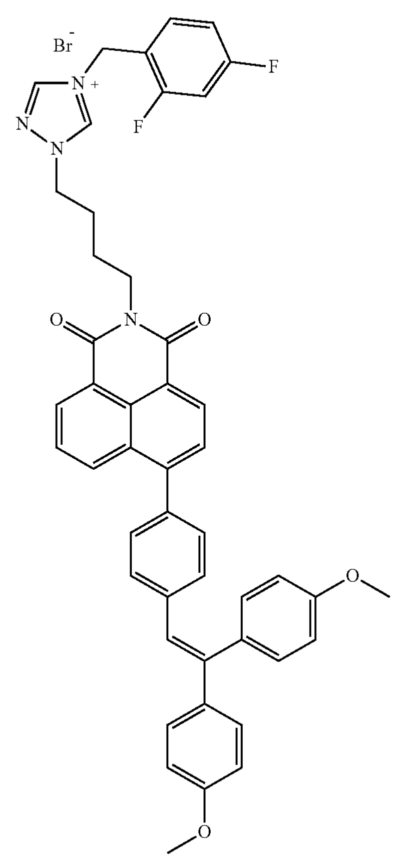

2. A pharmaceutical composition comprising the antibiotic compound of claim 1 and a pharmaceutically acceptable carrier.

3. The pharmaceutical composition of claim 2, wherein the pharmaceutically acceptable carrier is a topical carrier.

4. A method of treating a bacterial infection in a patient, comprising:

administering the compound of claim 1 to a site of an infection in a patient; and illuminating the site of the infection to generate reactive oxygen species from the compound of claim 1.

5. The method of treating a bacterial infection in a patient according to claim 4, wherein the site of the infection is illuminated with light for a duration of time in the range of 2 minutes to 30 minutes.

6. The method of treating a bacterial infection in a patient according to claim 4, wherein the illuminating comprises illuminating with white light.

7. A method of generating reactive oxygen species, comprising:

administering the compound of claim 1 to a portion of an object; and illuminating the portion of the object.

8. The method of generating reactive oxygen species according to claim 7, wherein the portion of the object is illuminated with white light for a duration of time in the range of 2 minutes to 30 minutes.

9. A method of imaging antibiotic interaction with bacteria, comprising:

administering the compound of claim 1 to a bacterial infection; and imaging the bacterial infection to view fluorescence produced from aggregation of the compound of claim 1.

* * * * *